(12) United States Patent
Vojkovsky et al.

(10) Patent No.: US 12,415,825 B2
(45) Date of Patent: Sep. 16, 2025

(54) MANUFACTURE OF TRANS-[TETRACHLOROBIS (1H-INDAZOLE)RUTHENATE (III)] AND COMPOSITIONS THEREOF

(71) Applicant: Bold Therapeutics, Inc., Vancouver (CA)

(72) Inventors: Tomas Vojkovsky, Palm Beach Gardens, FL (US); Kevin Sill, Tampa, FL (US); Adam Carie, Tampa, FL (US)

(73) Assignee: Bold Therapeutics, Inc., Vancouver (CA)

( * ) Notice: Subject to any disclaimer, the term of this patent is extended or adjusted under 35 U.S.C. 154(b) by 0 days.

(21) Appl. No.: 18/355,945

(22) Filed: Jul. 20, 2023

(65) Prior Publication Data
US 2023/0357297 A1 Nov. 9, 2023

Related U.S. Application Data

(60) Division of application No. 17/330,822, filed on May 26, 2021, now Pat. No. 11,739,111, which is a continuation of application No. 16/781,060, filed on Feb. 4, 2020, now Pat. No. 11,040,993, which is a division of application No. 15/973,370, filed on May 7, 2018, now Pat. No. 10,611,787.

(60) Provisional application No. 62/501,984, filed on May 5, 2017.

(51) Int. Cl.
| C07F 15/00 | (2006.01) |
| A61K 9/00 | (2006.01) |
| A61K 9/19 | (2006.01) |
| A61K 33/24 | (2019.01) |
| A61K 33/243 | (2019.01) |
| A61K 47/12 | (2006.01) |
| A61K 47/26 | (2006.01) |
| A61P 35/02 | (2006.01) |

(52) U.S. Cl.
CPC ........ *C07F 15/0053* (2013.01); *A61K 9/0019* (2013.01); *A61K 9/19* (2013.01); *A61K 33/24* (2013.01); *A61K 33/243* (2019.01); *A61K 47/12* (2013.01); *A61K 47/26* (2013.01); *A61P 35/02* (2018.01)

(58) Field of Classification Search
CPC .............................. C07F 15/0053; A61P 35/02
See application file for complete search history.

(56) References Cited

U.S. PATENT DOCUMENTS

| 8,362,266 B2 | 1/2013 | Keppler | |
| 10,611,787 B2 | 4/2020 | Vojkovsky et al. | |
| 11,040,993 B2 * | 6/2021 | Vojkovsky | A61K 47/26 |
| 11,739,111 B2 * | 8/2023 | Vojkovsky | A61K 47/12 |
| | | | 514/186 |
| 2005/0032801 A1 | 2/2005 | Keppler | |
| 2010/0094019 A1 | 4/2010 | Keppler | |
| 2013/0129840 A1 | 5/2013 | Sheshbaradaran et al. | |

FOREIGN PATENT DOCUMENTS

| CN | 103601759 | 2/2014 |
| JP | 2013531065 | 8/2013 |
| RU | 2015144121 | 4/2017 |
| WO | WO-9736595 A2 | 10/1997 |
| WO | WO-2008154553 A1 | 12/2008 |
| WO | WO-2012012305 A2 | 1/2012 |
| WO | WO-2014145428 A2 | 9/2014 |
| WO | WO-2016/209918 A1 | 12/2016 |

OTHER PUBLICATIONS

Bijelic et al., "X-ray Structure Analysis of Indazolium trans-[Tetrachlorobis(1H-indazole)ruthenate(III)] (KP1019) Bound to Human Serum Albumin Reveals Two Ruthenium Binding Sites and Provides Insights into the Drug Binding Mechanism," Journal of Medicinal Chemistry, 59, pp. 5894-5903 (2016).
Cebrian-Losantos et al., "Synthesis and Reactivity of the Aquation Product of the Antitumor Complex trans-[Ru(III)C14(indazole)2]-," Inorganic Chemistry, 47(14) pp. 6513-6523 (2008).
International Search Report for International Application No. PCT/US2018/031436 mailed Jun. 10, 2013 (4 pages).
Kobayashi et al. "Cesium reversibly suppresses HeLa cell proliferation by inhibiting cellular metabolism," Federation of European Biochemical Societies Letters, 591, pp. 718-727 (2017).
Mestroni et al., "Water-soluble Ruthenium(III)-Dimethyl Sulfoxide Complexes: Chemical Behaviour and Pharmaceutical Properties," Metal Based Drugs, pp. 41-63 (1993).
Motswainyana et al., "Anticancer Activities of Mononuclear Ruthenium(II) Coordination Complexes," Advances in Chemistry, Article ID 859730, pp. 1-21 (2015).
Thota et al. "Synthesis, antineoplastic and cytotoxic activities of some mononuclear Ru(II) comglexes," Journal of Enzyme Inhibition and Medicinal Chemistry, 25(4), pp. 513-519 (2010).
Peti et al. (Sep. 1999) "Synthesis of Tumor-Inhibiting Complex Salts Containing the Anion trans-Tetrachlorobis(indazole)ruthenate(III) and Crystal Structure of the Tetraphenylphosphonium Salt", European Journal of Inorganic Chemistry, 1999(9):1551-1555.

* cited by examiner

*Primary Examiner* — Golam M Shameem
(74) *Attorney, Agent, or Firm* — Mintz, Levin, Cohn, Ferris, Glovsky and Popeo, P.C.

(57) ABSTRACT

The present invention relates to the preparation of compositions comprising sodium trans-[tetrachlorobis(1H-indazole)ruthenate (III)]. Synthesis and formulation preparation is detailed. Impurity profiles are also discussed. Compositions herein are useful for anti-cancer applications.

9 Claims, 7 Drawing Sheets

MANUFACTURE OF TRANS-[TETRACHLOROBIS (1H-INDAZOLE)RUTHENATE (III)] AND COMPOSITIONS THEREOF

CROSS REFERENCE TO RELATED APPLICATIONS

This application is a divisional application of U.S. patent application Ser. No. 17/330,822, filed May 26, 2021, which is a continuation of U.S. patent application Ser. No. 16/781,060, filed Feb. 4, 2020, which is a divisional of U.S. patent application Ser. No. 15/973,370, filed May 7, 2018, which claims the benefit of priority to U.S. Provisional Patent Application No. 62/501,984, filed May 5, 2017, each of which is incorporated herein in its entirety for all purposes by reference.

FIELD OF THE INVENTION

This invention generally relates to chemical synthesis, and particularly relates to a method of making an alkali metal salt of trans-[tetrachlorobis(1H-indazole)ruthenate (III)].

BACKGROUND OF THE INVENTION

Several methods for the preparation of sodium trans-[tetrachlorobis(1H-indazole)ruthenate (III)](also known as KP1339, NKP-1339, IT-139, and Na[Ru$^{III}$Cl$_4$(Hind)$_2$]) exist in the literature. For example, W. Peti et al, *Eur. J. Inorg. Chem.* 1999, 1551-1555 discloses the following synthesis scheme.

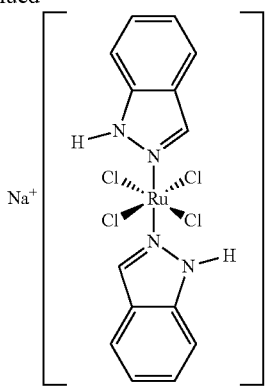

In this method, limited solubility of the tetramethylammoniumchloride salt results in a requirement for high volumes of solvent. Furthermore, there are toxicity concerns regarding the use of tetramethylammonium salts. An additional process is described in U.S. Pat. No. 8,362,266. This process provides a method of making the compound M-trans-[tetrachlorobis(1H-indazole)ruthenate (III)], wherein M is an alkali metal cation, said method comprising the steps of: (1) reacting, in an aqueous solution or a mixture of water and a first organic solvent which is water soluble, indazolium trans-[tetrachlorobis(1H-indazole)ruthenate (III)] with an inorganic salt of said alkali metal cation M, to form the compound M-trans-[tetrachlorobis(1H-indazole) ruthenate (III)] and an inorganic salt of indazole; and (2) extracting said indazole from said M-trans-[tetrachlorobis (1H-indazole)ruthenate (III)] with a second organic solvent which is not substantially water soluble. This method is summarized in the scheme below.

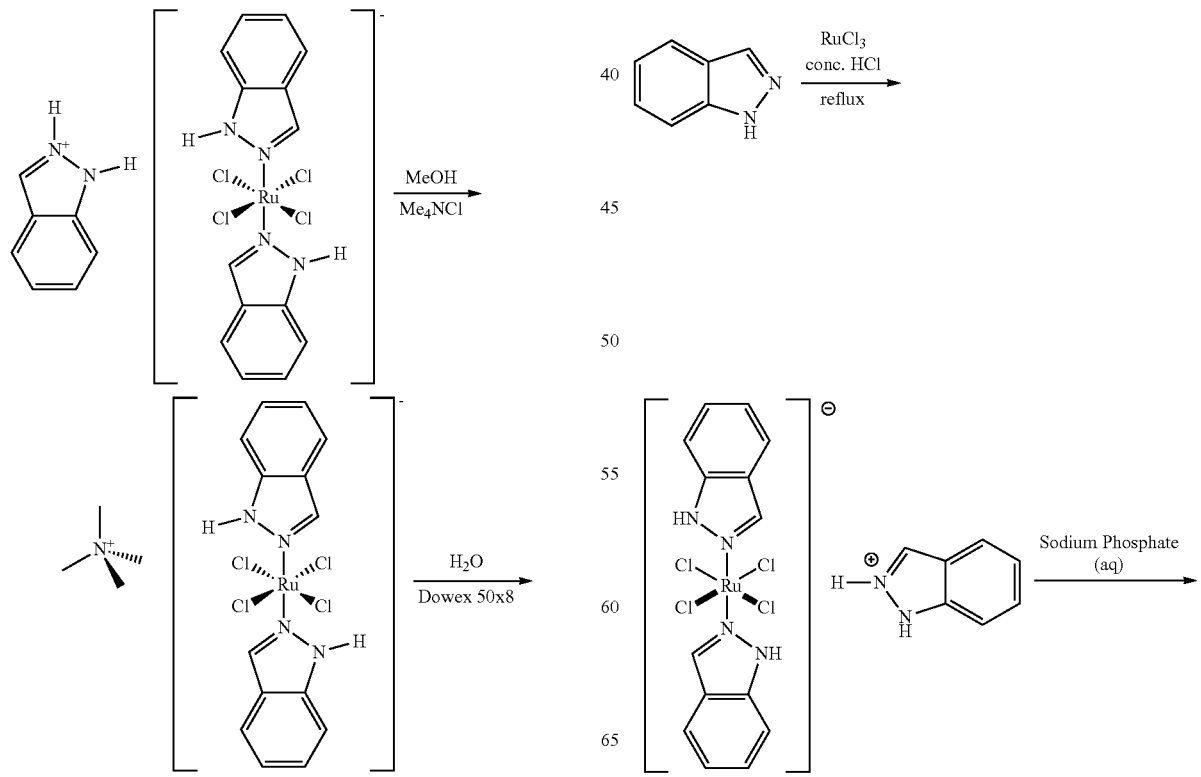

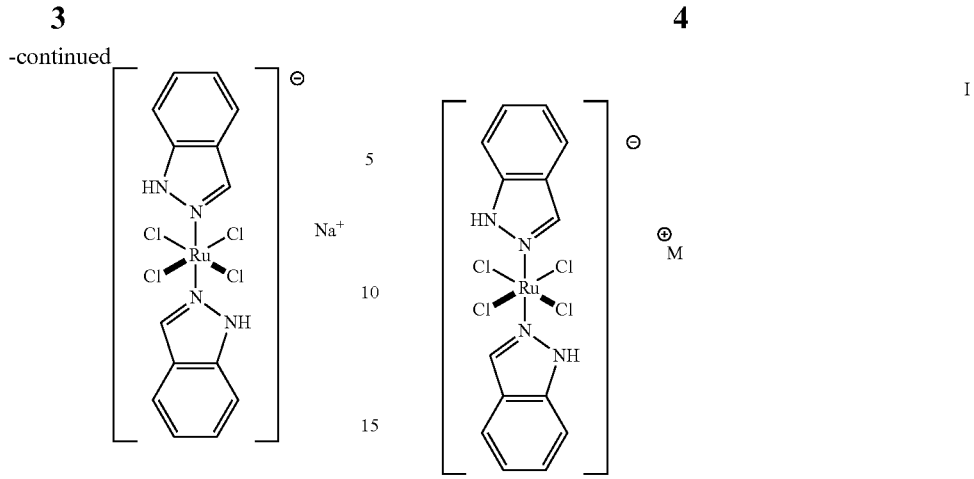

The method described above is effective; however, the need for the extraction step and related hold times may limit the effective batch size. Also, the purity of the compound is directly related to the length of time that the compound is in the basic, aqueous environment. Overall yields for this method are in the 20-35%. Therefore, a method that does not utilize an extraction process, avoids an aqueous basic environment, is high yielding and produces compound with high purity levels is highly desirable. Furthermore, a methodology that avoids extraction and large amounts of organic solvents is also desirable. A methodology primarily focused on precipitation followed by filtration would satisfy this need.

DETAILED DESCRIPTION OF CERTAIN EMBODIMENTS OF THE INVENTION

1. General Description

Figure 1:
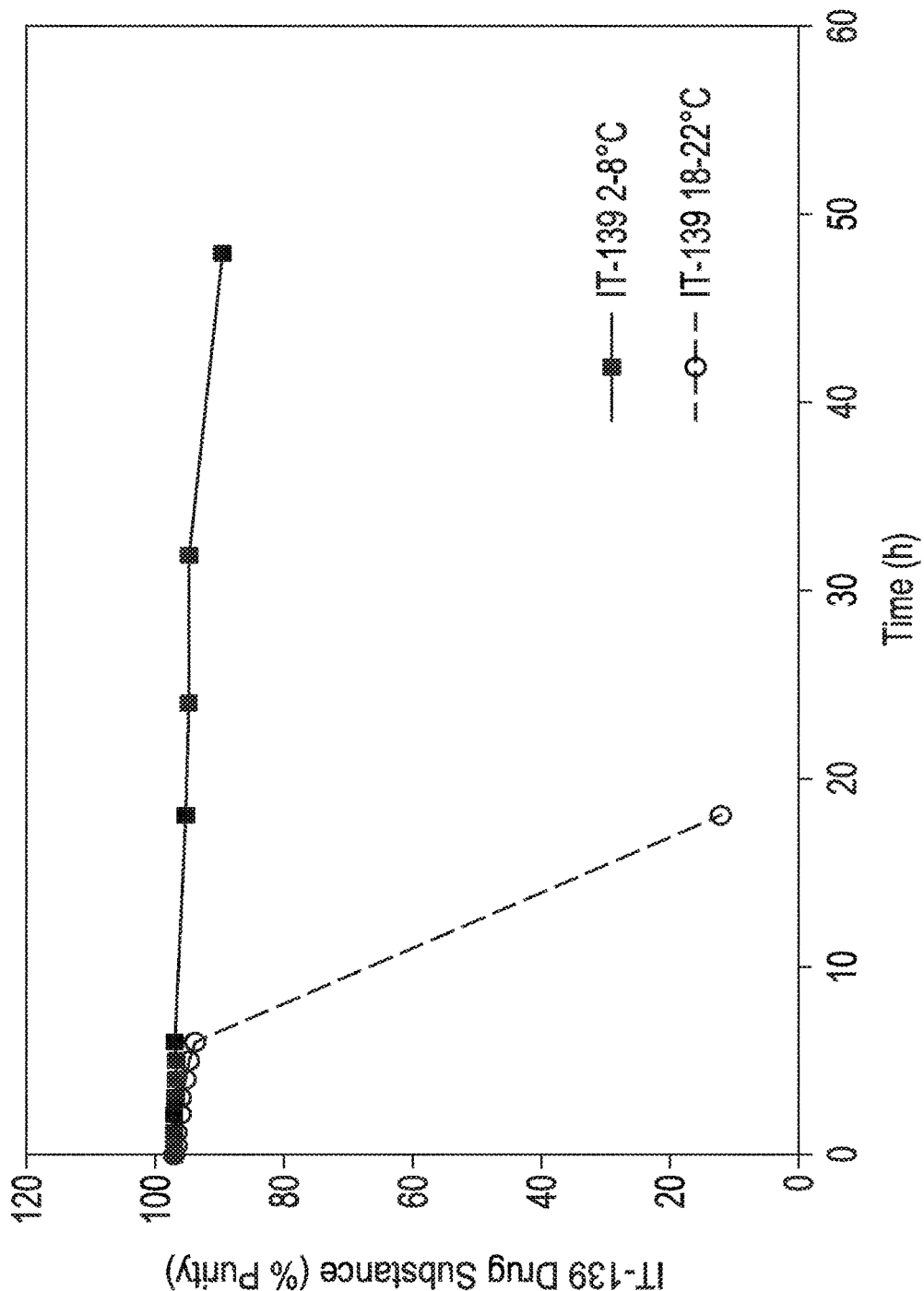
FIG. 1. Purity of IT-139 drug substance in bulk solution prepared and stored refrigerated (2-8° C.) and at room temperature (18-22° C.).

As described herein, the present invention provides methods for preparing alkali metal salts of trans-[tetrachlorobis (1H-indazole)ruthenate (III)]. Such compounds include those of Formula I.

wherein M is an alkali metal cation.

The present invention provides synthetic intermediates useful for preparing such compounds.

The present invention also provides methods for the preparation of cesium trans-[tetrachlorobis(1H-indazole)ruthenate (III)] as depicted in Formula I-a below.

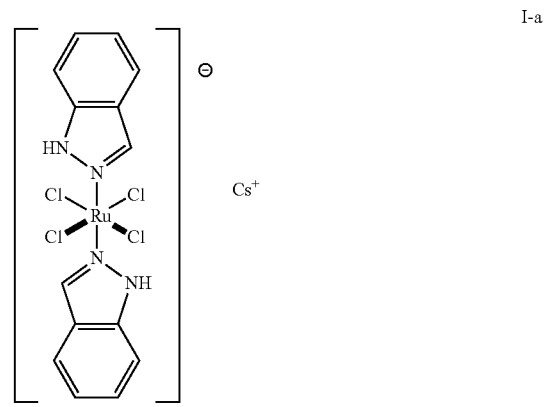

The present invention also provides methods for the preparation of sodium trans-[tetrachlorobis(1H-indazole)ruthenate (III)] as depicted in Formula I-b below.

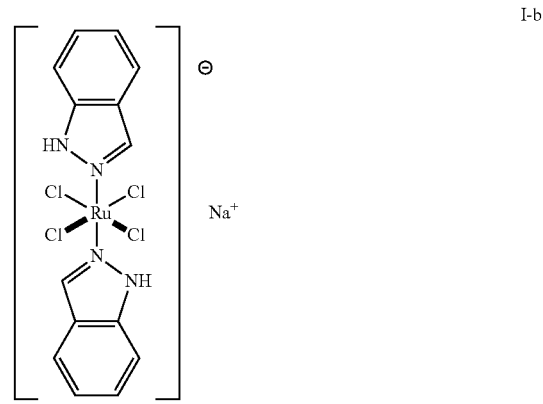

2. Definitions

It is understood that the terms sodium trans-[tetrachlorobis(1H-indazole)ruthenate (III)], KP1339, NKP-1339, IT-139, and Na[Ru$^{III}$Cl$_4$(Hind)$_2$] all represent the same compound (Formula I-b) and may be used interchangeably.

As used herein, the term amorphous refers to a non-crystalline solid that lacks long-range order.

Compounds of this invention include those described generally above, and are further illustrated by the embodiments, sub-embodiments, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments aliphatic groups contain 1-4 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon. This includes any oxidized form of nitrogen, sulfur, phosphorus, or silicon; the quaternized form of any basic nitrogen, or; a substitutable nitrogen of a heterocyclic ring including =N— as in 3,4-dihydro-2H-pyrrolyl, —NH— as in pyrrolidinyl, or =N(R†)—as in N-substituted pyrrolidinyl.

The term "unsaturated", as used herein, means that a moiety has one or more units of unsaturation.

As used herein, the term "bivalent, saturated or unsaturated, straight or branched $C_{1-12}$ hydrocarbon chain", refers to bivalent alkylene, alkenylene, and alkynylene chains that are straight or branched as defined herein.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains three to seven ring members. The term "aryl" may be used interchangeably with the term "aryl ring".

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Monovalent substituents on a substitutable carbon atom of an "optionally substituted" group are independently halogen; —(CH$_2$)$_{0-4}$R°; —(CH$_2$)$_{0-4}$OR°; —O—(CH$_2$)$_{0-4}$C(O) OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S) R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$—SC(O)R°; —(CH$_2$)$_{0-4}$C(O)NR°$_2$; —C(S) NR°2; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Monovalent substituents on R° (or the ring formed by taking two independent occurrences of R° together with their intervening atoms), are independently halogen, —(CH$_2$)$_{0-2}$R•, -(haloR•), —(CH$_2$)$_{0-2}$OH, —(CH$_2$)$_{0-2}$OR•, —(CH$_2$)$_{0-2}$CH(OR•)$_2$; —O(haloR•), —CN, —N$_3$, —(CH$_2$)$_{0-2}$C(O)R•, —(CH$_2$)$_{0-2}$C(O)OH, —(CH$_2$)$_{0-2}$C(O) OR•, —(CH$_2$)$_{0-2}$SR•, —(CH$_2$)$_{0-2}$SH, —(CH$_2$)$_{0-2}$NH$_2$, —(CH$_2$)$_{0-2}$NHR•, —(CH$_2$)$_{0-2}$NR•$_2$, —NO$_2$, —SiR•$_3$, —OSiR•$_3$, —C(O)SR•, —(C$_{1-4}$ straight or branched alkylene)C(O)OR•, or —SSR• wherein each R• is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Such divalent substituents on a saturated carbon atom of R° include =O and =S.

Divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. A tetravalent substituent that is bound to vicinal substitutable methylene carbons of an "optionally substituted" group is the dicobalt hexacarbonyl cluster represented by

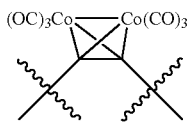

when depicted with the methylenes which bear it.

Suitable substituents on the aliphatic group of R* include halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†2, —C(O)R†, —C(O)OR†, —C(O)C(O)R†, —C(O)CH$_2$C(O)R†, —S(O)$_2$R†, —S(O)$_2$NR†$_2$, —C(S)N R†$_2$, —C(NH) NR†$_2$, or —N(R†)S(O)$_2$R†; wherein each R† is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Protected hydroxyl groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably protected hydroxyl groups further include, but are not limited to, esters, carbonates, sulfonates allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benylbenzoate, 2,4,6-trimethylbenzoate. Examples of carbonates include 9-fluorenylmethyl, ethyl, 2,2,2-trichloroethyl, 2-(trimethylsilyl) ethyl, 2-(phenylsulfonyl)ethyl, vinyl, allyl, and p-nitrobenzyl carbonate. Examples of silyl ethers include trimethylsilyl, triethylsilyl, t-butyldimethylsilyl, t-butyldiphenylsilyl, triisopropylsilyl ether, and other trialkylsilyl ethers. Examples of alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Mono-protected amines further include, but are not limited to, aralkylamines, carbamates, allyl amines, amides, and the like. Examples of mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Di-protected amines include amines that are substituted with two substituents independently selected from those described above as mono-protected amines, and further include cyclic imides, such as phthalimide, maleimide, succinimide, and the like. Di-protected amines also include pyrroles and the like, 2,2,5,5-tetramethyl-[1,2,5]azadisilolidine and the like, and azide.

Protected aldehydes are well known in the art and include those described in detail in Greene (1999). Protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional protected carboxylic acids include oxazolines and ortho esters.

Protected thiols are well known in the art and include those described in detail in Greene (1999). Protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as in neutron scattering experiments, as analytical tools or probes in biological assays.

The expression "unit dosage form" as used herein refers to a physically discrete unit of inventive formulation appropriate for the subject to be treated. It will be understood, however, that the total daily usage of the compositions of the present invention will be decided by the attending physician within the scope of sound medical judgment. The specific effective dose level for any particular subject or organism will depend upon a variety of factors including the disorder being treated and the severity of the disorder; activity of specific active agent employed; specific composition employed; age, body weight, general health, sex and diet of the subject; time of administration, and rate of excretion of the specific active agent employed; duration of the treatment; drugs and/or additional therapies used in combination or coincidental with specific compound(s) employed, and like factors well known in the medical arts.

The term "about" when referring to a measurable value such as an amount, a temporal duration, and the like, refers to variations of ±20% or in some instances ±10%, or in some instances ±5%, or in some instances ±1%, or in some instances ±0.1% from the specified value, as such variations are appropriate to perform the disclosed methods.

3. Description of Exemplary Embodiments 3.1 Drug Substance

In certain embodiments, the present compounds are generally prepared according to Scheme I set forth below:

Scheme I

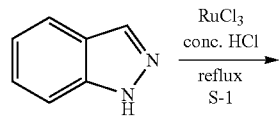

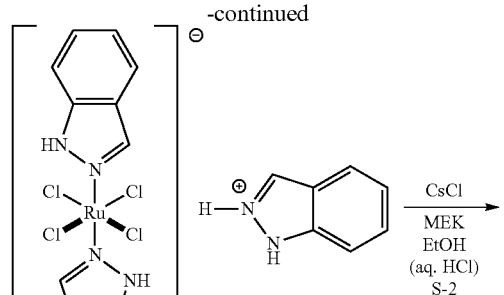

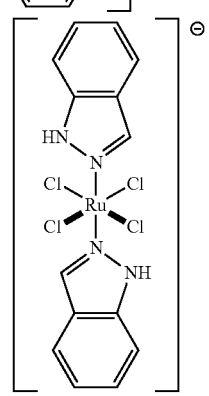

I-a

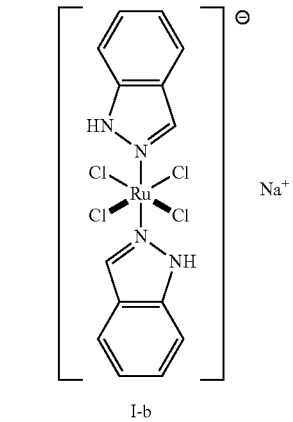

I-b

In one aspect, the present invention provides methods for preparing compounds of Formula I according to the steps depicted in Scheme I above. In step S-1, ruthenium (III) chloride is reacted with indazole to form the indazolium salt of trans-[tetrachlorobis(1H-indazole)ruthenate (III)]. This step (S-1) is well known in the art, see Keppler et. al. *Inorganic Chemistry*, 26, 1987. At step S-2, the indazolium salt is converted to the cesium salt of trans-[tetrachlorobis (1H-indazole)ruthenate (III)], Formula I-a, by treatment with cesium chloride. One skilled in the art will recognize this as a salt exchange from the indazolium salt to the cesium salt. At step S-3, the cesium salt of Formula I-a is converted to the sodium salt of trans-[tetrachlorobis(1H-indazole)ruthenate (III)], Formula I-b, by treatment with sodium aluminium sulphate. One skilled in the art will recognize this as a salt exchange from the cesium salt to the sodium salt.

In certain embodiments, each of the aforementioned synthetic steps may be performed sequentially with isolation of each intermediate performed after each step. Alternatively, each of steps S-1, S-2, and S-3, as depicted in Scheme I above, may be performed in a manner whereby no isolation of intermediates is performed.

One of ordinary skill in the art will recognize that the steps S-1, S-2, and S-3 involve the preparation of first the indazolium salt, then the cesium salt, then the sodium salt of trans-[tetrachlorobis(1H-indazole)ruthenate (III)]. Furthermore, U.S. Pat. No. 8,362,266 describes the preparation of Formula I-b directly from the indazolium salt. One aspect of the present invention includes the preparation of Formula I-a as an intermediate in the synthesis of Formula I-b. It was discovered that the cesium salt intermediate is preferred over existing methods because product purity and overall yield can be significantly increased over existing methods. Without wishing to be bound to any particular theory, we believe the reason for this increase in yield and purity is due to the difficulty in isolating the indazolium salt of trans-[tetrachlorobis(1H-indazole)ruthenate (III)]. We have found that this material is very difficult to isolate as pure substance free of solvent, as the filtered material possesses residual water and hydrochloric acid. One proposed degradation pathway of the material is shown in Scheme II below.

Scheme II

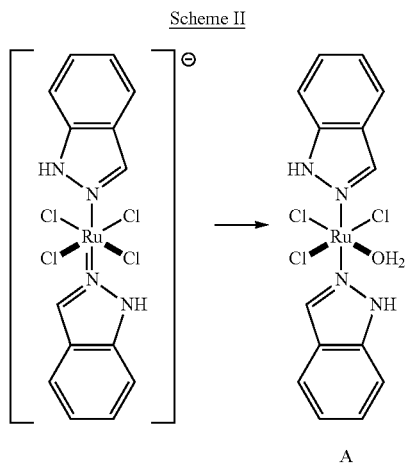

A

Scheme II shows the preparation of compound A (mer, trans-[Ru$^{III}$Cl$_3$(Hind)$_2$(H$_2$O)], which results from the displacement of a chlorine atom by a water molecule. The impurity, Compound A, is also known as the aqua complex in the literature. The production of compound A can be limited by exclusion of water or maintaining an appreciably high concentration of chloride ions. For example, Formula I-b is much more stable in sodium chloride or hydrochloric acid solutions than pure water. One skilled in the art will recognize that maintaining a concentration of chloride ions reduces the chances of displacement of a chloride on the ruthenium complex by water. Furthermore, it was discovered that the rate of aquation (or preparation of Compound A) is greatly increased in basic solutions.

Because the primary degradation product is an aquation reaction, particularly one that is accelerated in basic aqueous solutions, it would be preferable to avoid reaction steps that involve dissolving compounds of Formula I in water.

One embodiment of the invention provides a method of preparing Formula I-b by preparing indazolium trans-[tetrachlorobis(1H-indazole)ruthenate (III)], isolating the material by filtration, drying until the material is 200%-500% by mass of theoretical yield for use in S-2. In other embodiments, the invention provides a method of preparing Formula I-b by preparing indazolium trans-[tetrachlorobis(1H-indazole)ruthenate (III)], isolating the material by filtration, drying until the material is 245%-425% by mass of theoretical yield for use in S-2.

Another aspect of the invention is the introduction of step S-2 into the preparation of Formula I-b. Step S-2 involves the preparation of a cesium intermediate, Formula I-a. The cesium intermediate was surprisingly found to be a critical step of the present invention because it can be isolated by precipitation and filtration, can be dried without inducing degradation (as observed with the indazolium salt), and the dry powder is stable at ambient conditions. As stated above, indazolium trans-[tetrachlorobis(1H-indazole)ruthenate (III)] is isolated by filtration as what can best be described as a mud-like substance. The stability of this compound is improved by the presence of hydrochloric acid (chloride ions). Washing the filtrate with polar solvents (e.g. methanol) also lead to degradation. Therefore, the best practice is to prepare the indazolium trans-[tetrachlorobis(1H-indazole)ruthenate (III)], isolate by filtration, and use directly for S-2 without delay. S-2 consists of mixing indazolium trans-[tetrachlorobis(1H-indazole)ruthenate (III)] and cesium chloride in a suitable solvent. Suitable solvents can be alcohol with 1 to 5 carbon atoms, a diol with 2-4 carbon atoms, water, ketones with 1 to 6 carbon atoms, cyclic ethers containing 4 to 7 carbon atoms, amides with 1 to 4 carbon atoms, DMSO, sulfolane, esters with 4 to 6 carbon atoms, chlorinated hydrocarbons with 1 or 2 carbon atoms, liquid aromatic hydrocarbons, nitriles with 2-6 carbon atoms, or mixture of thereof.

In one aspect of the present invention, S-2 consists of mixing indazolium trans-[tetrachlorobis(1H-indazole)ruthenate (III)] and cesium chloride in ethanol and methyl ethyl ketone to provide Formula I-a. The cesium salt intermediate was collected by filtering the reaction mixture and washing with ethanol. In some embodiments, S-2 utilizes 1-10 equivalents of cesium chloride in the reaction mixture. In other embodiments, S-2 utilizes 2-4 equivalents of cesium chloride in the reaction mixture. In the preferred embodiment, the present invention provides a method of preparing Formula I-b, wherein 2.8 equivalents of cesium chloride are used in step S-2. Preferred solvents for S-2 are ethanol-containing mixtures, and the most preferred are ethanol-methyl ethyl ketone (MEK) mixtures, due their ability to form a crystalline MEK solvate of the cesium salt, which aids the purification. The obtained MEK solvate in this case is afterwards readily transformed to a more stable hydrate form of cesium salt, by a treatment with aqueous ethanol.

Another aspect of the invention is step S-3 which converts the cesium salt intermediate (Formula I-a) into the desired sodium salt, Formula I-b. Previous methodologies to provide Formula I-b, described herein, include treatment of an aqueous solution of trans-[tetrachlorobis(1H-indazole)ruthenate (III)] with a sodium salt under basic conditions. As described above, the aqueous, basic conditions lead to degradation into Compound A. To address this issue, we developed step S-3 which converts Formula I-a into Formula I-b by mixing with sodium aluminium sulfate (NaAl(SO$_4$)$_2$). This salt exchange was performed by mixing sodium aluminium sulfate and Formula I-a in water. The reaction is performed at high concentration such that the reaction mixture is heterogeneous. The driving force for the reaction is the differential solubilities of sodium aluminium sulfate and cesium aluminium sulfate. Sodium aluminium sulfate is soluble in water and provides a source of sodium ions. Cesium aluminium sulfate is insoluble in water, and precipitates out of the reaction mixture. Therefore, the cesium counterion is continually removed from the reaction solution, resulting in the formation of Formula I-b. The insoluble cesium aluminium sulfate and Formula I-b are isolated by filtration. Formula I-b is dissolved in a suitable solvent and the cesium aluminium sulfate is removed by filtration. Suitable solvents include low molecular weight alcohols (with 1 to 5 carbon atoms), ketones with 3 to 6 carbon atoms, nitriles with 2 to 5 carbon atoms, esters with 3 to 6 carbon atoms, amides with 1 to 4 carbon atoms, water, diols with 1 to 4 carbon atoms, DMSO, sulfolane, water, or a combination of thereof. The most preferred solvent for solid extraction is acetonitrile. Formula I-b is then precipitated with a suitable anti-solvent and recovered by filtration. Suitable anti-solvents include ethers with 3 to 8 carbon atoms, cyclic, acyclic or aromatic hydrocarbons with 5 to 8 carbon atoms, chlorinated hydrocarbons with 1 to 4 carbon atoms, benzotrifluoride, chlorobenzene, methyl carbonate. The most preferred antisolvent is methyl tert-butyl ether (MTBE).

In some embodiments, the present invention provides a method of preparing Formula I-b, wherein the concentration of sodium aluminum sulfate in step S-3 is 0.5 M to 1.65 M. In the preferred embodiment, the present invention provides a method of preparing Formula I-b, wherein the concentration of sodium aluminum sulfate in step S-3 is 1.1 M.

In some embodiments, the present invention provides a method of preparing Formula I-b, wherein the reaction temperature of step S-3 is from −5° C. to 50° C. In the preferred embodiment, the present invention provides a method of preparing Formula I-b, wherein the reaction temperature of step S-3 is from 20° C. to 25° C.

In some embodiments, the present invention provides a method of preparing Formula I-b, wherein the reaction time of step S-3 is from 12 hours to 168 hours. In the preferred embodiment, the present invention provides a method of preparing Formula I-b, wherein the reaction time of step S-3 is 30 hours.

Yet another aspect of the invention is a purification step in which residual cesium is removed from Formula I-b. This process involves stirring Formula I-b in the presence of 4 Å molecular sieves with methanol, followed by precipitation with MTBE. Without wishing to be bound to any particular theory, it is believed that cesium atoms have an affinity for the 4 Å pores present in the molecular sieves. Furthermore, it was discovered that trace solvent impurities can be removed from the desired product by stirring and washing with an MTBE solution that is saturated with water. Use of this final purification step affords the highest purity Formula I-b.

Characterization of the ruthenium containing target compounds required multiple techniques. Nuclear magnetic resonance spectroscopy of the ruthenium compounds is difficult due to the 5/2 nuclear spin state, thus alternative characterization methods were employed, including HPLC and x-ray diffraction (crystallography). In order to fully characterize the purity of IT-139, we purposefully prepared a number of compounds believed to be impurities in the final composition of IT-139, namely Compounds A, C, and D. The identity of the impurities A, C, and D was confirmed by x-ray diffraction. Compound B is an unstable complex believed to be an intermediate in the formation of Compound C. The structure of the impurity compounds are as follows:

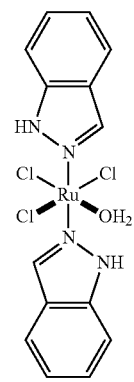

A

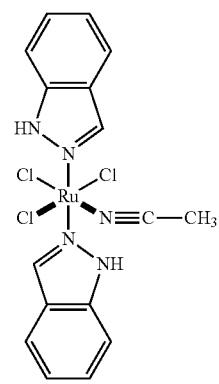

B

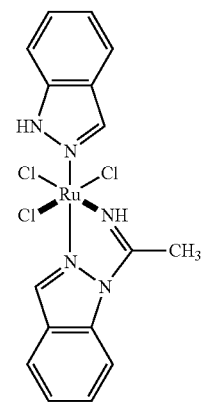

C

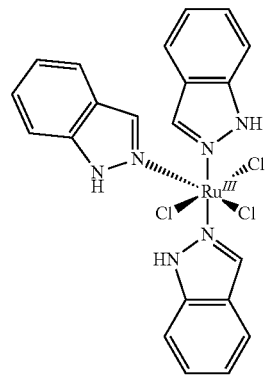

D

Once the impurity compounds were prepared and identified, their retention times were analyzed by HPLC, such that the identity and percentage of impurity could be quickly quantified by HPLC analysis. During this process, we observed that the aqua complex, Compound A, resulted in multiple peaks on the HPLC, and that chromatographic profile would change as a function of time. It was discovered that the aqua complex was reacting with the acetonitrile in the mobile phase to form an acetonitrile adduct, Compound B, and that this adduct was subsequently reacting to form a covalent derivative with acetonitrile, Compound C. (See Inorganic Chemistry, 2008, v47, p 6513-6523). This reaction is depicted in Scheme III below.

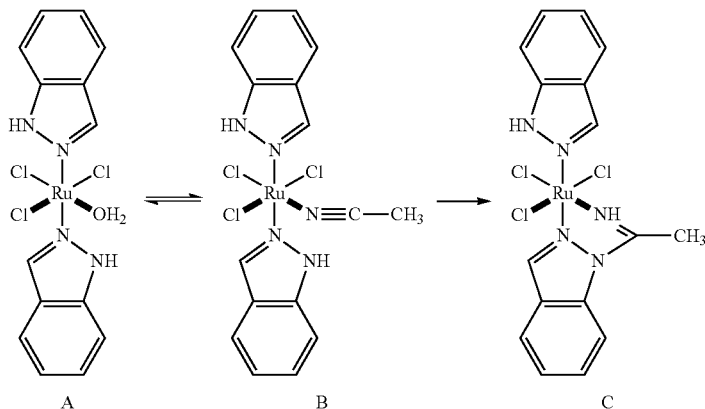

The relative retention times for each compound are listed in the Table below (Table 1):

TABLE 1

HPLC relative retention times for Formula I-b, Compound A, Compound B, Compound C, and Compound D.

| Complex | Compound Label | RRT |
|---|---|---|
| $Ru^{III}Cl_3(Hind)_2(H_2O)$ | Compound A | 1.10 |
| $Ru^{III}Cl_3(Hind)(HN=C(Me)ind)$ | Compound C | 1.07 |
| $Ru^{III}Cl_3(Hind)_2(CH_3CN)$ | Compound B | 1.28 |
| $Ru^{III}Cl_3(Hind)_3$ | Compound D | 1.59 |
| $Na[Ru^{III}Cl_4(Hind)_2]$ | Formula I-b | 1.0 |

In some embodiments, the relative retention times (RRT) described in Table 1 can be defined by a range. For instance, the RRT of Compound A can be 1.09+/−0.02, the RRT of Compound B can be 1.28+/−0.02, the RRT of Compound C can be 1.06+/−0.03, and the RRT of Compound D can be 1.59+/−0.03.

Because the aqua complex (Compound A) will rapidly form compounds B and C in the mobile phase for HPLC analysis, the amount of Compound A in a sample submitted for HPLC analysis is determined to be the sum of the peak areas corresponding to Compounds A, B, and C. One benefit of the synthetic methodology of present invention over other synthetic methodologies is the high purity level that can be achieved by the present invention. Previous methodologies described above provide a final product (drug substance) containing 4-8% of Compound A as an impurity. As a comparison, less than 2% of compound A is readily achievable with the present invention. One embodiment of the present invention provides a composition comprising sodium trans-[tetrachlorobis(1H-indazole)ruthenate (III)] and Compound A, wherein there is no more than 2.0% by weight Compound A in the composition. One embodiment of the present invention provides a composition comprising sodium trans-[tetrachlorobis(1H-indazole)ruthenate (III)] and Compound A, wherein there is no more than 1.0% by weight Compound A in the composition. One embodiment of the present invention provides a composition comprising sodium trans-[tetrachlorobis(1H-indazole)ruthenate (III)] and Compound A, wherein there is no more than 1.5% by weight Compound A in the composition. One embodiment of the present invention provides a composition comprising sodium trans-[tetrachlorobis(1H-indazole)ruthenate (III)] and Compound A, wherein there is no more than 0.5% by weight Compound A in the composition. One embodiment of the present invention provides a composition comprising sodium trans-[tetrachlorobis(1H-indazole)ruthenate (III)] and Compound A, wherein there is no more than 3.0% by weight Compound A in the composition.

Figure 4:
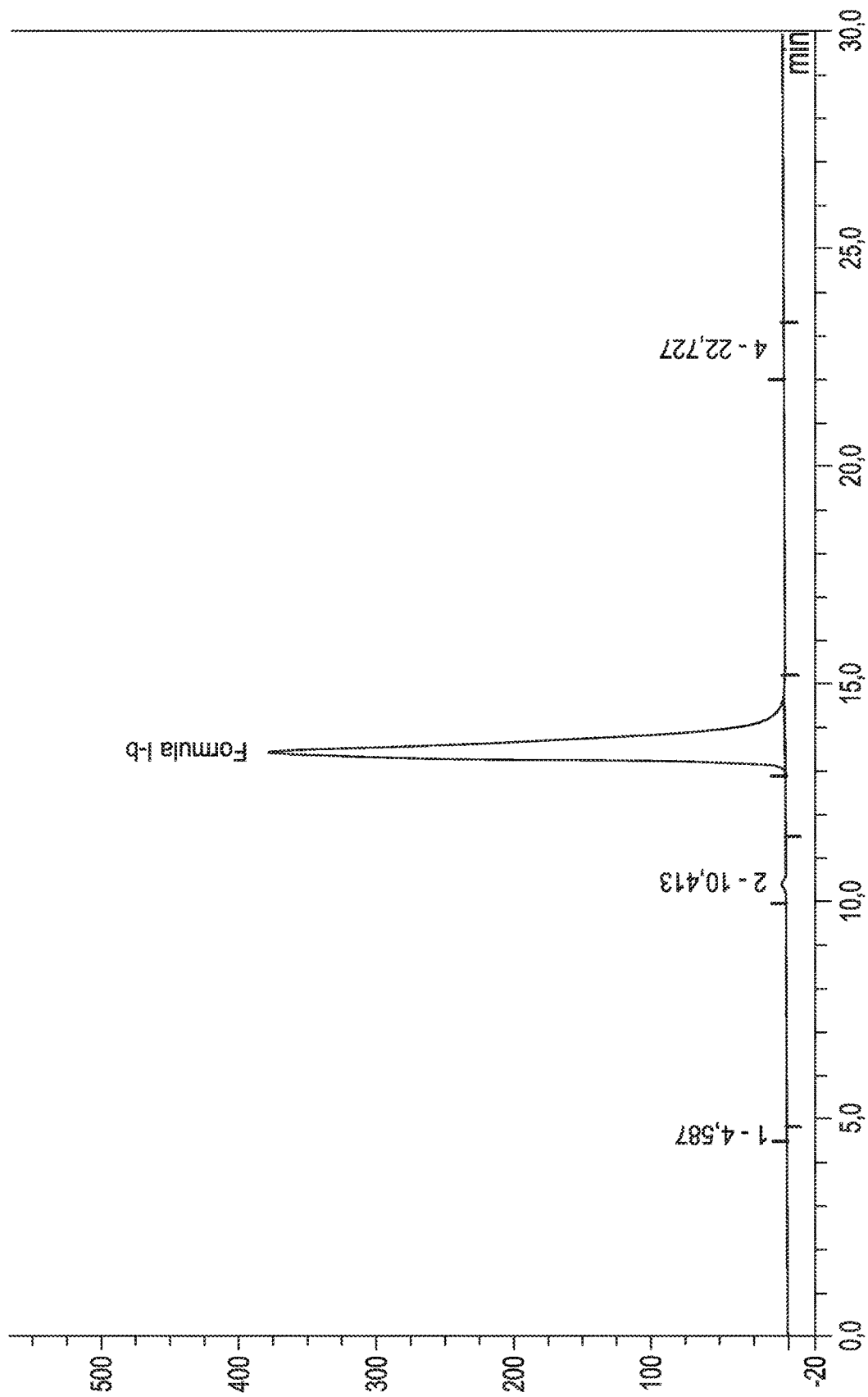
Figure 5:
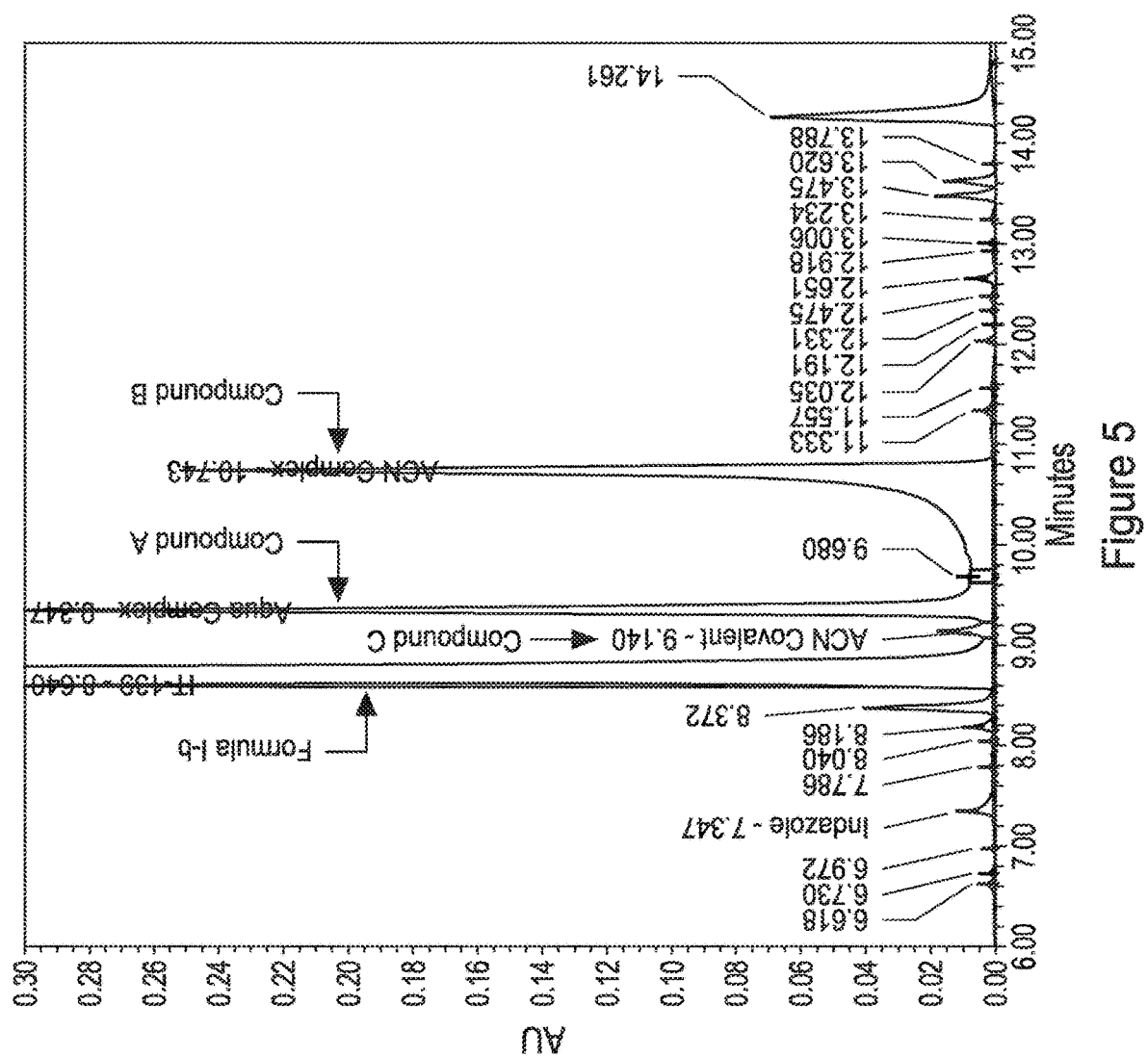
FIG. 5. HPLC chromatogram ising HPLC Method #2 of Formula I-b prepared using previous synthetic method.
Figure 6:
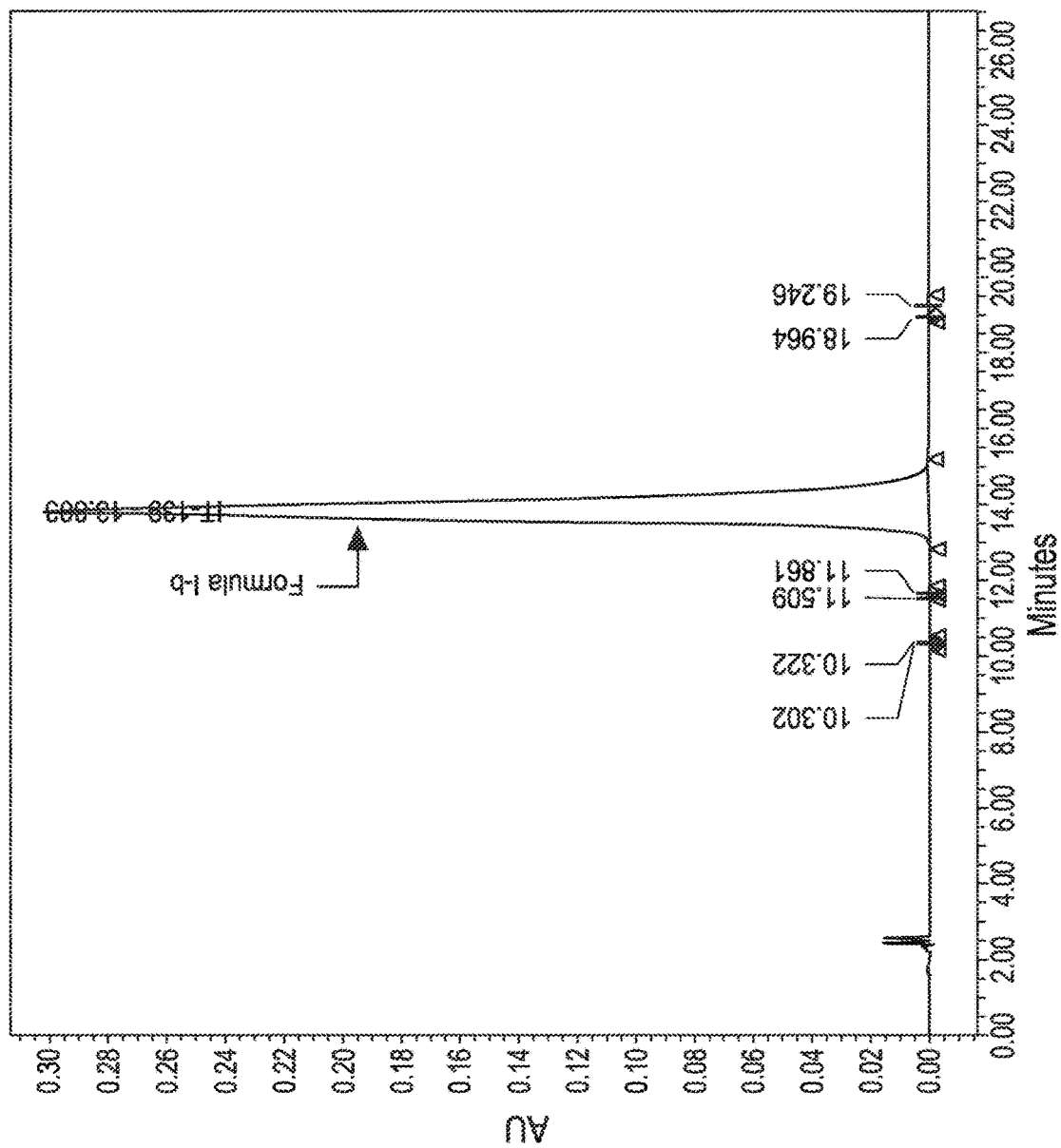
FIG. 6. HPLC chromatogram using HPLC Method #3 of Formula I-b prepared using the synthetic methodology of the present invention.
Figure 7:
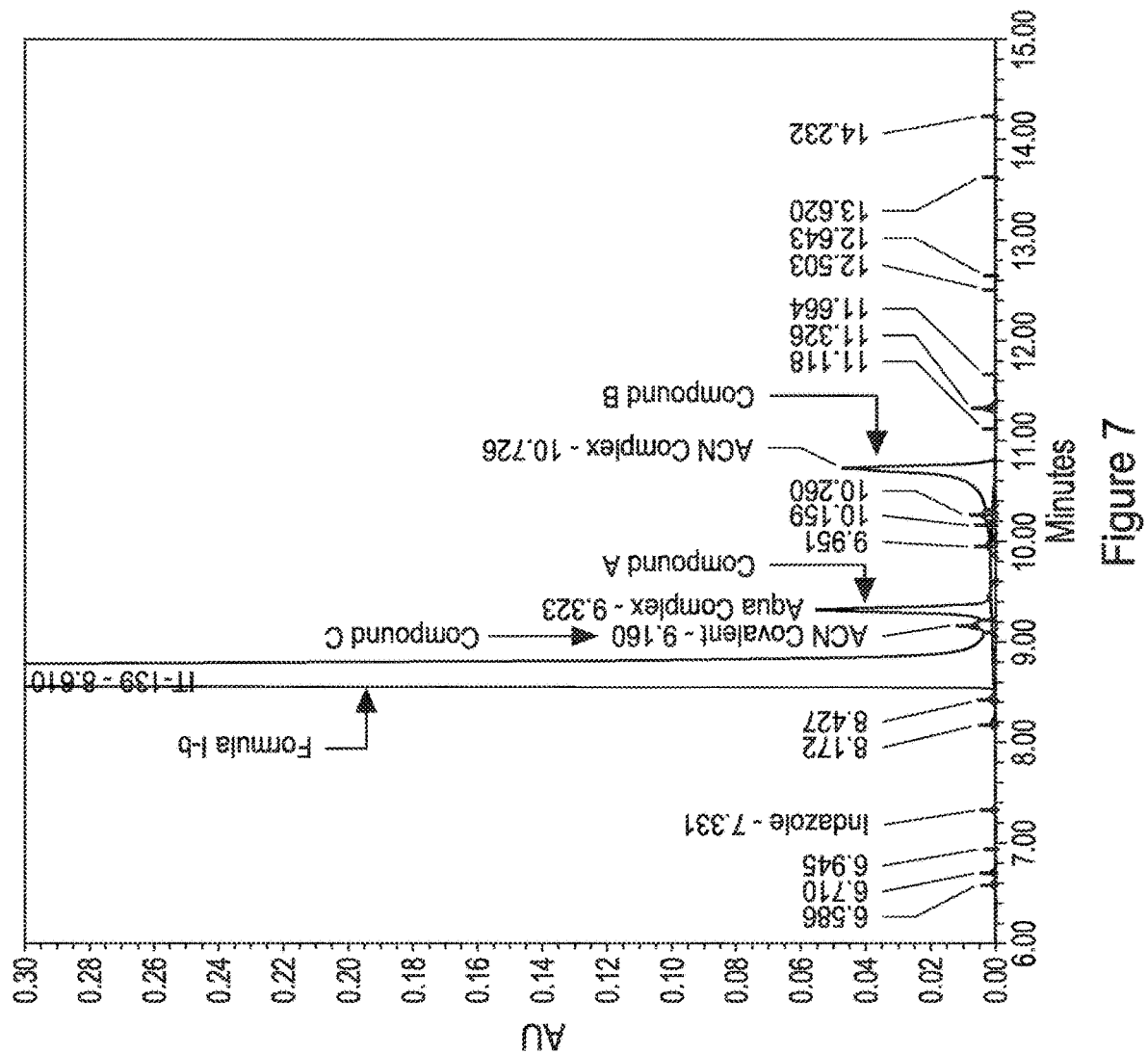
FIG. 7. HPLC chromatogram using HPLC Method #2 of Formula I-b prepared using the synthetic methodology of the present invention.

Another benefit of the present invention over previous synthetic methodologies is a reduction in the amounts of impurities produced. Previous synthetic methodologies described above (see, e.g., U.S. Pat. No. 8,362,266) were often analyzed using an HPLC method (e.g. HPLC Method #3, vide infra) that did not resolve the impurities (Compound A, Compound B, and Compound C) from the drug substance (Formula I-b). FIG. 4 illustrates the drug substance prepared using other synthetic methodologies analyzed using HPLC Method #3, while FIG. 5 illustrates the same drug substance analyzed using an analytical method (HPLC Method #2, vide infra) which resolves Formula I-b from impurities Compound A, Compound B, and Compound C. Consequently, drug substance synthesized using other methodologies reported a purity of about 99.5% (analyzed with HPLC Method #3), however, the same material analyzed using HPLC Method #2 demonstrated that the purity was actually approximately about 76.4% Formula I-b contaminated with about 7.3% Compound A, about 11.0% Compound B, and about 0.36% Compound C. The present invention provides a composition comprising Formula I-b in a purity of about 99.9% as analyzed with the HPLC Method #3. The present invention provides a composition comprising about 96.3% Formula I-b, about 1.1% Compound A, about 1.7% Compound B, and about 0.2% Compound C. The HPLC data is reproduced in the table below (Table 2).

TABLE 2

HPLC Analysis of Formula I-b, Compound A, Compound B, and Compound C prepared using the present invention and the previous synthetic method.

| Synthesis Method | Analysis Method | Formula I-b (area %) | Impurities | | |
|---|---|---|---|---|---|
| | | | Compound A (area %) | Compound B (area %) | Compound C (area %) |
| Previous methodology | HPLC Method #3 | 99.5 | n/a[1] | n/a[1] | n/a[1] |
| Previous methodology | HPLC Method #2 | 76.4 | 7.3 | 11.0 | 0.36 |
| Present Invention | HPLC Method #3 | 99.9 | n/a[1] | n/a[1] | n/a[1] |
| Present Invention | HPLC Method #2 | 96.3 | 1.1 | 1.7 | 0.2 |

[1]Impurities not resolved from Formula I-b

One embodiment of the present invention provides a composition comprising sodium trans-[tetrachlorobis(1H-indazole)ruthenate (III)], $Ru^{III}Cl_3(Hind)_2(H_2O)$, $Ru^{III}Cl_3(Hind)_2(CH_3CN)$, and $Ru^{III}Cl_3(Hind)(HN=C(Me)ind)$.

One embodiment of the present invention provides a composition comprising sodium trans-[tetrachlorobis(1H-indazole)ruthenate (III)], $Ru^{III}Cl_3(Hind)_2(H_2O)$, $Ru^{III}Cl_3(Hind)_2(CH_3CN)$, $Ru^{III}Cl_3(Hind)(HN=C(Me)ind)$ and cesium.

One embodiment of the present invention provides a composition comprising sodium trans-[tetrachlorobis(1H-indazole)ruthenate (III)], $Ru^{III}Cl_3(Hind)_2(H_2O)$, $Ru^{III}Cl_3(Hind)_2(CH_3CN)$, and $Ru^{III}Cl_3(Hind)(HN=C(Me)ind)$, and cesium,
wherein:
the sodium trans-[tetrachlorobis(1H-indazole)ruthenate (III)] is not less than about 95.5 weight percentage of the composition,
the $Ru^{III}Cl_3(Hind)_2(H_2O)$ is not more than about 1.0 weight percentage of the composition,
the $Ru^{III}Cl_3(Hind)_2(CH_3CN)$ is not more than about 2.5 weight percentage of the composition,
the $Ru^{III}Cl_3(Hind)(HN=C(Me)ind)$ is not more than about 2.0 weight percentage of the composition,
and cesium is not more than about 0.5 weight percentage of the composition.

One embodiment of the present invention provides a composition comprising sodium trans-[tetrachlorobis(1H-indazole)ruthenate (III)], cesium, and optionally $Ru^{III}Cl_3(Hind)_2(H_2O)$, $Ru^{III}Cl_3(Hind)_2(CH_3CN)$, and $Ru^{III}Cl_3(Hind)(HN=C(Me)ind)$:
wherein:
the sodium trans-[tetrachlorobis(1H-indazole)ruthenate (III)] is between about 95.5 and about 99.9 weight percentage of the composition,
the $Ru^{III}Cl_3(Hind)_2(H_2O)$ is between about 0 and about 1.0 weight percentage of the composition, the $Ru^{III}Cl_3(Hind)_2(CH_3CN)$ is between about 0 and about 2.5 weight percentage of the composition,
the $Ru^{III}Cl_3(Hind)(HN=C(Me)ind)$ is between about 0 and 2.0 about weight percentage of the composition,
and cesium is between about 0 and about 0.5 weight percentage of the composition.

One embodiment of the present invention provides a composition comprising sodium trans-[tetrachlorobis(1H-indazole)ruthenate (III)], $Ru^{III}Cl_3(Hind)_2(H_2O)$, $Ru^{III}Cl_3(Hind)_2(CH_3CN)$, and $Ru^{III}Cl_3(Hind)(HN=C(Me)ind)$, and cesium,
wherein:
the sodium trans-[tetrachlorobis(1H-indazole)ruthenate (III)] is between about 95.5 and about 99.9 weight percentage of the composition,
the $Ru^{III}Cl_3(Hind)_2(H_2O)$ is between about 0.001 and about 1.0 weight percentage of the composition,
the $Ru^{III}Cl_3(Hind)_2(CH_3CN)$ is between about 0.001 and about 2.5 weight percentage of the composition,
the $Ru^{III}Cl_3(Hind)(HN=C(Me)ind)$ is between about 0.001 and 2.0 about weight percentage of the composition,
and cesium is between about 0.0001 and about 0.5 weight percentage of the composition.

One embodiment of the present invention provides a composition comprising sodium trans-[tetrachlorobis(1H-indazole)ruthenate (III)], $Ru^{III}Cl_3(Hind)_2(H_2O)$, $Ru^{III}Cl_3(Hind)_2(CH_3CN)$, and $Ru^{III}Cl_3(Hind)(HN=C(Me)ind)$, and cesium,
wherein:
the sodium trans-[tetrachlorobis(1H-indazole)ruthenate (III)] is between about 95.5 and about 99.9 weight percentage of the composition,
the $Ru^{III}Cl_3(Hind)_2(H_2O)$ is between about 0.001 and about 0.75 weight percentage of the composition,
the $Ru^{III}Cl_3(Hind)_2(CH_3CN)$ is between about 0.001 and about 1.5 weight percentage of the composition,
the $Ru^{III}Cl_3(Hind)(HN=C(Me)ind)$ is between about 0.001 and 1.25 about weight percentage of the composition,
and cesium is between about 0.0001 and about 0.25 weight percentage of the composition.

One embodiment of the present invention provides a composition comprising sodium trans-[tetrachlorobis(1H-indazole)ruthenate (III)], $Ru^{III}Cl_3(Hind)_2(H_2O)$, $Ru^{III}Cl_3(Hind)_2(CH_3CN)$, and $Ru^{III}Cl_3(Hind)(HN=C(Me)ind)$, and cesium,
wherein:
the sodium trans-[tetrachlorobis(1H-indazole)ruthenate (III)] is between about 95.5 and about 99.9 weight percentage of the composition,
the $Ru^{III}Cl_3(Hind)_2(H_2O)$ is between about 0.001 and about 0.5 weight percentage of the composition,
the $Ru^{III}Cl_3(Hind)_2(CH_3CN)$ is between about 0.001 and about 0.5 weight percentage of the composition,
the $Ru^{III}Cl_3(Hind)(HN=C(Me)ind)$ is between about 0.001 and 0.5 about weight percentage of the composition,
and cesium is between about 0.0001 and about 0.01 weight percentage of the composition.

3.2 Drug Product

Additional embodiments of the present invention provide methods for preparing drug products containing the sodium salt of trans-[tetrachlorobis(1H-indazole)ruthenate (III)](i.e. IT-139).

One aspect of the current invention provides a method for preparing a sterile, lyophilized drug product containing sodium trans-[tetrachlorobis(1H-indazole)ruthenate (III)]. This formulation would be suitable for administration to a patient. The formulation is comprised of sodium trans-[tetrachlorobis(1H-indazole)ruthenate (III)], a pH buffer, and a cryoprotective agent. The general method for providing said formulation comprises the steps of preparing aqueous buffer solution, preparing aqueous cryoprotectant solution, dissolution of sodium trans-[tetrachlorobis(1H-indazole)ruthenate (III)] in the buffer solution, addition of the cryoprotectant solution, sterile filtration (e.g. aseptic filtration), filling of vials under sterile conditions, and lyophilization under sterile conditions. Suitable buffers include, but are not limited to: citrate, TRIS, acetate, EDTA, HEPES, tricine, and imidazole. The use of a phosphate buffer is possible but is not preferred. A preferred aspect of the present invention is the use of a citric acid/sodium citrate buffer. Suitable cryoprotective agents include, but are not limited to: sugars, monosaccarides, disaccharides, polyalcohols, mannitol, sorbitol, sucrose, trehalose, dextran, and dextrose. A preferred aspect of the present invention is the use of mannitol as the cyroprotecive agent.

As described above, herein, sodium trans-[tetrachlorobis (1H-indazole)ruthenate (III)] can degrade in water to Compound A (Scheme II). One skilled in the art will recognize that limiting this degradation reaction would be advantageous to obtaining the highest purity product. It was found that cooling the sodium trans-[tetrachlorobis(1H-indazole) ruthenate (III)] solution during the formulation process was found to greatly reduce the amount of Compound A present in the lyophilized product. In one aspect of the invention, the sodium trans-[tetrachlorobis(1H-indazole)ruthenate (III)] solution is cooled to 4° C. during the formulation process. In another aspect of the invention, the sodium trans-[tetrachlorobis(1H-indazole)ruthenate (III)] solution is cooled to 2-8° C. during the formulation process. In another aspect of the invention, the sodium trans-[tetrachlorobis(1H-indazole)ruthenate (III)] solution is cooled to 2-15° C. during the formulation process.

One embodiment of the present invention provides a composition comprising sodium trans-[tetrachlorobis(1H-indazole)ruthenate (III)], a suitable buffer, and mannitol. In some embodiments, a suitable buffer comprises a citrate buffer. For instance, in some embodiments, a citrate buffer comprises sodium citrate and citric acid.

One embodiment of the present invention provides a composition comprising sodium trans-[tetrachlorobis(1H-indazole)ruthenate (III)], sodium citrate, citric acid, and mannitol.

One embodiment of the present invention provides a composition comprising sodium trans-[tetrachlorobis(1H-indazole)ruthenate (III)], sodium citrate, citric acid, mannitol, and mer,trans-[Ru$^{III}$Cl$_3$(Hind)$_2$(H$_2$O)].

One embodiment of the present invention provides a composition comprising sodium trans-[tetrachlorobis(1H-indazole)ruthenate (III)], sodium citrate, citric acid, mannitol, mer,trans-[Ru$^{III}$Cl$_3$(Hind)$_2$(H$_2$O)], and a cesium salt.

One embodiment of the present invention provides a composition comprising sodium trans-[tetrachlorobis(1H-indazole)ruthenate (III)], sodium citrate, citric acid, and mannitol, wherein the sodium trans-[tetrachlorobis(1H-indazole)ruthenate (III)] is amorphous.

One embodiment of the present invention provides a composition comprising sodium trans-[tetrachlorobis(1H-indazole)ruthenate (III)], sodium citrate, citric acid, mannitol, and mer,trans-[Ru$^{III}$Cl$_3$(Hind)$_2$(H$_2$O)], wherein the sodium trans-[tetrachlorobis(1H-indazole)ruthenate (III)] is amorphous.

One embodiment of the present invention provides a composition comprising sodium trans-[tetrachlorobis(1H-indazole)ruthenate (III)], sodium citrate, citric acid, mannitol, mer,trans-[Ru$^{III}$Cl$_3$(Hind)$_2$(H$_2$O)], and a cesium salt, wherein the sodium trans-[tetrachlorobis(1H-indazole)ruthenate (III)] is amorphous.

One embodiment of the present invention provides a composition comprising sodium trans-[tetrachlorobis(1H-indazole)ruthenate (III)], sodium citrate, citric acid, mannitol, mer,trans-[Ru$^{III}$Cl$_3$(Hind)$_2$(H$_2$O)], and a cesium salt;
  wherein:
    mer,trans-[Ru$^{III}$Cl$_3$(Hind)$_2$(H$_2$O)] is between about 0.01 and about 0.4 weight percent of the composition,
    and cesium is between about 0.00001 and about 0.01 weight percent of the composition.

One embodiment of the present invention provides a composition comprising sodium trans-[tetrachlorobis(1H-indazole)ruthenate (III)], sodium citrate, citric acid, mannitol, mer,trans-[Ru$^{III}$Cl$_3$(Hind)$_2$(H$_2$O)], and a cesium salt;
  wherein:
    mer,trans-[Ru$^{III}$Cl$_3$(Hind)$_2$(H$_2$O)] is between about 0.01 and about 0.4 weight percent of the composition,
    and cesium is between about 0.00001 and about 0.01 weight percent of the composition.

One embodiment of the present invention provides a composition comprising sodium trans-[tetrachlorobis(1H-indazole)ruthenate (III)], sodium citrate, citric acid, mannitol, mer,trans-[Ru$^{III}$Cl$_3$(Hind)$_2$(H$_2$O)], and a cesium salt;
  wherein:
    mer,trans-[Ru$^{III}$Cl$_3$(Hind)$_2$(H$_2$O)] is between about 0.01 and about 0.2 weight percent of the composition,
    and cesium is between about 0.00001 and about 0.01 weight percent of the composition.

One embodiment of the present invention provides a composition comprising sodium trans-[tetrachlorobis(1H-indazole)ruthenate (III)], mer,trans-[Ru$^{III}$Cl$_3$(Hind)$_2$(H$_2$O)], and a cesium salt;
  wherein:
    mer,trans-[Ru$^{III}$Cl$_3$(Hind)$_2$(H$_2$O)] is between about 0.01 and about 0.40 weight percent of the composition,
    and cesium is between about 0.00001 and about 0.01 weight percent of the composition.

One embodiment of the present invention provides a composition comprising sodium trans-[tetrachlorobis(1H-indazole)ruthenate (III)], mer,trans-[Ru$^{III}$C$_3$(Hind)$_2$(H$_2$O)], and a cesium salt;
  wherein:
    the composition is a lyophilized powder,
    mer,trans-[Ru$^{III}$Cl$_3$(Hind)$_2$(H$_2$O)] is between about 0.01 and about 0.40 weight percent of the composition,
    and cesium is between about 0.00001 and about 0.01 weight percent of the composition.

One embodiment of the present invention provides a composition comprising sodium trans-[tetrachlorobis(1H-indazole)ruthenate (III)], sodium citrate, citric acid, mannitol, mer,trans-[Ru$^{III}$Cl$_3$(Hind)$_2$(H$_2$O)], and a cesium salt;

wherein:
the composition is a lyophilized powder,
mer,trans-[Ru$^{III}$Cl$_3$(Hind)$_2$(H$_2$O)] is between about 0.01 and about 0.3 weight percent of the composition,
and cesium is between about 0.00001 and about 0.1 weight percent of the composition.

One embodiment of the present invention provides a composition comprising sodium trans-[tetrachlorobis(1H-indazole)ruthenate (III)], sodium citrate, citric acid, mannitol, mer,trans-[Ru$^{III}$Cl$_3$(Hind)$_2$(H$_2$O)], and a cesium salt;
wherein:
mer,trans-[Ru$^{III}$Cl$_3$(Hind)$_2$(H$_2$O)] is between about 0.01 and about 0.3 weight percent of the composition,
and cesium is between about 0.00001 and about 0.1 weight percent of the composition.

One embodiment of the present invention provides a composition comprising sodium trans-[tetrachlorobis(1H-indazole)ruthenate (III)], sodium citrate, citric acid, mannitol, mer,trans-[Ru$^{III}$Cl$_3$(Hind)$_2$(H$_2$O)], and a cesium salt;
wherein:
the composition is a lyophilized powder,
sodium trans-[tetrachlorobis(1H-indazole)ruthenate (III)] is about 11.5 to about 14.0 weight percent of the composition,
citric acid is about 43.9 to about 53.7 weight percent of the composition,
sodium citrate is about 25.7 to about 23.1 weight percent of the composition,
mannitol is about 11.5 to about 14.0 weight percent of the composition,
mer,trans-[Ru$^{III}$Cl$_3$(Hind)$_2$(H$_2$O)] is about 0.01 and about 0.3 weight percent of the composition,
and cesium is between about 0.00001 and about 0.1 weight percent of the composition.

One embodiment of the present invention provides a composition comprising sodium trans-[tetrachlorobis(1H-indazole)ruthenate (III)], sodium citrate, citric acid, mannitol, mer,trans-[Ru$^{III}$Cl$_3$(Hind)$_2$(H$_2$O)], and a cesium salt;
wherein:
the composition is a lyophilized powder,
sodium trans-[tetrachlorobis(1H-indazole)ruthenate (III)] is about 10.2 to about 15.3 weight percent of the composition,
citric acid is about 39.0 to about 58.5 weight percent of the composition,
sodium citrate is about 20.5 to about 30.8 weight percent of the composition,
mannitol is about 10.2 to about 15.3 weight percent of the composition,
mer,trans-[Ru$^{III}$Cl$_3$(Hind)$_2$(H$_2$O)] is about 0.01 and about 0.3 weight percent of the composition,
and cesium is between about 0.00001 and about 0.1 weight percent of the composition.

One embodiment of the present invention provides a composition comprising sodium trans-[tetrachlorobis(1H-indazole)ruthenate (III)], sodium citrate, citric acid, mannitol, mer,trans-[Ru$^{III}$Cl$_3$(Hind)$_2$(H$_2$O)], and a cesium salt;
wherein:
the composition is a lyophilized powder,
sodium trans-[tetrachlorobis(1H-indazole)ruthenate (III)] is about 10.2 to about 15.3 weight percent of the composition,
mer,trans-[Ru$^{III}$Cl$_3$(Hind)$_2$(H$_2$O)] is about 0.01 and about 0.3 weight percent composition,
and cesium is between about 0.00001 and about 0.1 weight percent of the composition.

One embodiment of the present invention provides a composition comprising sodium trans-[tetrachlorobis(1H-indazole)ruthenate (III)], mannitol, citric acid, and sodium citrate;
wherein:
sodium trans-[tetrachlorobis(1H-indazole)ruthenate (III)] is about 49.86 weight percent of the composition,
mannitol is about 49.86 weight percent of the composition,
citric acid is about 0.187 weight percent of the composition,
and sodium citrate is about 0.093 weight percentage of the composition. In some such embodiments, the composition is a lyophilized powder.

One embodiment of the present invention provides a composition comprising sodium trans-[tetrachlorobis(1H-indazole)ruthenate (III)], mannitol, citric acid, and sodium citrate;
wherein:
sodium trans-[tetrachlorobis(1H-indazole)ruthenate (III)] is about 40 to about 60 weight percent of the composition,
mannitol is about 40 to about 60 weight percent of the composition,
citric acid is about 0.01 to about 0.5 weight percent of the composition,
and sodium citrate is about 0.001 to about 0.25 weight percentage of the composition. In some such embodiments, the composition is a lyophilized powder.

One embodiment of the present invention provides a composition comprising sodium trans-[tetrachlorobis(1H-indazole)ruthenate (III)], mannitol, citric acid, and sodium citrate;
wherein:
sodium trans-[tetrachlorobis(1H-indazole)ruthenate (III)] is about 30 to about 70 weight percent of the composition,
mannitol is about 30 to about 70 weight percent of the composition,
citric acid is about 0.001 to about 1 weight percent of the composition,
and sodium citrate is about 0.0001 to about 1 weight percentage of the composition. In some such embodiments, the composition is a lyophilized powder.

One embodiment of the present invention provides a composition comprising sodium trans-[tetrachlorobis(1H-indazole)ruthenate (III)], mannitol, citric acid, sodium citrate, and Ru$^{III}$Cl$_3$(Hind)$_2$(H$_2$O);
wherein:
sodium trans-[tetrachlorobis(1H-indazole)ruthenate (III)] is about 49.86 weight percent of the composition,
mannitol is about 49.86 weight percent of the composition,
citric acid is about 0.187 weight percent of the composition,
sodium citrate is about 0.093 weight percentage of the composition,
and Ru$^{III}$Cl$_3$(Hind)$_2$(H$_2$O) is not more than 0.5 weight percentage of the composition. In some such embodiments, the composition is a lyophilized powder.

One embodiment of the present invention provides a composition comprising sodium trans-[tetrachlorobis(1H-indazole)ruthenate (III)], mannitol, citric acid, sodium citrate, and Ru$^{III}$Cl$_3$(Hind)$_2$(H$_2$O);

wherein:
sodium trans-[tetrachlorobis(1H-indazole)ruthenate (III)] is about 40 to about 60 weight percent of the composition,
mannitol is about 40 to about 60 weight percent of the composition,
citric acid is about 0.01 to about 0.5 weight percent of the composition,
sodium citrate is about 0.001 to about 0.25 weight percentage of the composition,
and $Ru^{III}Cl_3(Hind)_2(H_2O)$ is about 0 to about 0.5 weight percentage of the composition. In some such embodiments, the composition is a lyophilized powder.

One embodiment of the present invention provides a composition comprising sodium trans-[tetrachlorobis(11H-indazole)ruthenate (III)], mannitol, citric acid, sodium citrate, $Ru^{III}Cl_3(Hind)_2(H_2O)$, and cesium;
wherein:
sodium trans-[tetrachlorobis(1H-indazole)ruthenate (III)] is about 30 to about 70 weight percent of the composition,
mannitol is about 30 to about 70 weight percent of the composition,
citric acid is about 0.001 to about 1 weight percent of the composition,
sodium citrate is about 0.0001 to about 1 weight percentage of the composition,
$Ru^{III}Cl_3(Hind)_2(H_2O)$ is not more than 0.5 weight percentage of the composition,
and cesium is not more than 0.25 weight percentage of the composition. In some such embodiments, the composition is a lyophilized powder.

One embodiment of the present invention provides a composition comprising sodium trans-[tetrachlorobis(1H-indazole)ruthenate (III)], mannitol, citric acid, sodium citrate, and cesium;
wherein:
sodium trans-[tetrachlorobis(1H-indazole)ruthenate (III)] is about 49.61 weight percent of the composition,
mannitol is about 49.86 weight percent of the composition,
citric acid is about 0.187 weight percent of the composition,
sodium citrate is about 0.093 weight percentage of the composition
and cesium is about 0.25 weight percentage of the composition. In some such embodiments, the composition is a lyophilized powder.

One embodiment of the present invention provides a composition comprising sodium trans-[tetrachlorobis(1H-indazole)ruthenate (III)], mannitol, citric acid, sodium citrate, and cesium;
wherein:
sodium trans-[tetrachlorobis(1H-indazole)ruthenate (III)] is about 40 to about 60 weight percent of the composition,
mannitol is about 40 to about 60 weight percent of the composition,
citric acid is about 0.01 to about 0.5 weight percent of the composition,
sodium citrate is about 0.001 to about 0.25 weight percentage of the composition,
and cesium is about 0.1 to about 0.5 weight percentage of the composition. In some such embodiments, the composition is a lyophilized powder.

One embodiment of the present invention provides a composition comprising sodium trans-[tetrachlorobis(1H-indazole)ruthenate (III)], mannitol, citric acid, sodium citrate, and cesium;
wherein:
sodium trans-[tetrachlorobis(1H-indazole)ruthenate (III)] is about 30 to about 70 weight percent of the composition,
mannitol is about 30 to about 70 weight percent of the composition,
citric acid is about 0.001 to about 1 weight percent of the composition,
sodium citrate is about 0.0001 to about 1 weight percentage of the composition,
and cesium is about 0.01 to about 1 weight percentage of the composition. In some such embodiments, the composition is a lyophilized powder.

One embodiment of the present invention provides a composition comprising sodium trans-[tetrachlorobis(1H-indazole)ruthenate (III)], mannitol, citric acid, sodium citrate, $Ru^{III}Cl_3(Hind)_2(H_2O)$, $Ru^{III}Cl_3(Hind)_2(CH_3CN)$, $Ru^{III}Cl_3(Hind)(HN=C(Me)ind)$, and cesium; wherein:
sodium trans-[tetrachlorobis(1H-indazole)ruthenate (III)] about 46.61 weight percent of the composition,
mannitol is about 49.86 weight percent of the composition,
citric acid is about 0.187 weight percent of the composition,
sodium citrate is about 0.093 weight percentage of the composition,
$Ru^{III}Cl_3(Hind)_2(H_2O)$ is not more than 0.5 weight percentage of the composition,
$Ru^{III}Cl_3(Hind)_2(CH_3CN)$ is not more than 1.25 weight percentage of the composition,
$Ru^{III}Cl_3(Hind)(HN=C(Me)ind)$ is not more than 1.0 weight percentage of the composition,
and cesium is not more than 0.25 weight percentage of the composition. In some such embodiments, the composition is a lyophilized powder.

One embodiment of the present invention provides a composition comprising sodium trans-[tetrachlorobis(1H-indazole)ruthenate (III)], mannitol, citric acid, sodium citrate, $Ru^{III}Cl_3(Hind)_2(H_2O)$, $Ru^{III}Cl_3(Hind)_2(CH_3CN)$, $Ru^{III}Cl_3(Hind)(HN=C(Me)ind)$, and cesium;
wherein:
sodium trans-[tetrachlorobis(1H-indazole)ruthenate (III)] about between 46.61 weight percent of the composition,
mannitol is about 49.86 weight percent of the composition,
citric acid is about 0.187 weight percent of the composition,
sodium citrate is about 0.093 weight percentage of the composition,
$Ru^{III}Cl_3(Hind)_2(H_2O)$ is not more than 0.5 weight percentage of the composition,
$Ru^{III}Cl_3(Hind)_2(CH_3CN)$ is not more than 1.25 weight percentage of the composition,
$Ru^{III}Cl_3(Hind)(HN=C(Me)ind)$ is not more than 1.0 weight percentage of the composition,
and cesium is not more than 0.25 weight percentage of the composition. In some such embodiments, the composition is a lyophilized powder.

One embodiment of the present invention provides a composition comprising sodium trans-[tetrachlorobis(1H-indazole)ruthenate (III)], mannitol, citric acid, sodium citrate, $Ru^{III}Cl_3(Hind)_2(H_2O)$, $Ru^{III}Cl_3(Hind)_2(CH_3CN)$, $Ru^{III}Cl_3(Hind)(HN=C(Me)ind)$, and cesium;
wherein:
sodium trans-[tetrachlorobis(1H-indazole)ruthenate (III)] is about 40 to about 60 weight percent of the composition,
mannitol is about 40 to about 60 weight percent of the composition,
citric acid is about 0.01 to about 0.5 weight percent of the composition,
sodium citrate is about 0.001 to about 0.25 weight percentage of the composition,
$Ru^{III}Cl_3(Hind)_2(H_2O)$ is not more than about 0.5 weight percentage of the composition,
$Ru^{III}Cl_3(Hind)_2(CH_3CN)$ is not more than about 1.25 weight percentage of the composition,
$Ru^{III}Cl_3(Hind)(HN=C(Me)ind)$ is not more than about 1.0 weight percentage of the composition,
and cesium is not more than 0.25 percentage of the composition. In some such embodiments, the composition is a lyophilized powder.

One embodiment of the present invention provides a composition comprising sodium trans-[tetrachlorobis(1H-indazole)ruthenate (III)], mannitol, citric acid, sodium citrate, $Ru^{III}Cl_3(Hind)_2(H_2O)$, $Ru^{III}Cl_3(Hind)_2(CH_3CN)$, $Ru^{III}Cl_3(Hind)(HN=C(Me)ind)$, and cesium; wherein:
sodium trans-[tetrachlorobis(1H-indazole)ruthenate (III)] is about 30 to about 70 weight percent of the composition,
mannitol is about 30 to about 70 weight percent of the composition,
citric acid is about 0.001 to about 1 weight percent of the composition,
sodium citrate is about 0.0001 to about 1 weight percentage of the composition,
$Ru^{III}Cl_3(Hind)_2(H_2O)$ is not more than about 0.5 weight percentage of the composition,
$Ru^{III}Cl_3(Hind)_2(CH_3CN)$ is not more than about 1.25 weight percentage of the composition,
$Ru^{III}Cl_3(Hind)(HN=C(Me)ind)$ is not more than about 1.0 weight percentage of the composition,
and cesium is not more than 0.25 percentage of the composition. In some such embodiments, the composition is a lyophilized powder.

One embodiment of the present invention provides a composition comprising sodium trans-[tetrachlorobis(1H-indazole)ruthenate (III)], mannitol, citric acid, sodium citrate, $Ru^{III}Cl_3(Hind)_2(H_2O)$, $Ru^{III}Cl_3(Hind)_2(CH_3CN)$, $Ru^{III}Cl_3(Hind)(HN=C(Me)ind)$, and cesium; wherein:
sodium trans-[tetrachlorobis(1H-indazole)ruthenate (III)] is about 20 to about 80 weight percent of the composition,
mannitol is about 20 to about 80 weight percent of the composition,
citric acid is about 0.0001 to about 5 weight percent of the composition,
sodium citrate is about 0.00001 to about 5 weight percentage of the composition,
$Ru^{III}Cl_3(Hind)_2(H_2O)$ is not more than about 0.5 weight percentage of the composition,
$Ru^{III}Cl_3(Hind)_2(CH_3CN)$ is not more than about 1.25 weight percentage of the composition,
$Ru^{III}Cl_3(Hind)(HN=C(Me)ind)$ is not more than about 1.0 weight percentage of the composition,
and cesium is not more than 0.25 percentage of the composition. In some such embodiments, the composition is a lyophilized powder.

3.3 Unit Dosage Forms

In some embodiments, the present invention provides a unit dosage form comprising a formulation or composition described herein. The expression "unit dosage form" as used herein refers to a physically discrete unit of a provided formulation appropriate for the subject to be treated. It will be understood, however, that the total daily usage of provided formulation will be decided by the attending physician within the scope of sound medical judgment. The specific effective dose level for any particular subject or organism will depend upon a variety of factors including the disorder being treated and the severity of the disorder; activity of specific active agent employed; specific formulation employed; age, body weight, general health, sex and diet of the subject; time of administration, and rate of excretion of the specific active agent employed; duration of the treatment; drugs and/or additional therapies used in combination or coincidental with specific compound(s) employed, and like factors well known in the medical arts.

Compositions of the present invention can be provided as a unit dosage form. In some embodiments, a vial comprising sodium trans-[tetrachlorobis(1H-indazole)ruthenate (III)], mannitol, citric acid, sodium citrate is a unit dosage form.

In some embodiments, the present invention a vial comprising sodium trans-[tetrachlorobis(1H-indazole)ruthenate (III)], mannitol, citric acid, sodium citrate, and cesium is a unit dosage form.

In some embodiments, the present invention a vial comprising sodium trans-[tetrachlorobis(1H-indazole)ruthenate (III)], mannitol, citric acid, sodium citrate, $Ru^{III}Cl_3(Hind)_2(H_2O)$, $Ru^{III}Cl_3(Hind)_2(CH_3CN)$, $Ru^{III}Cl_3(Hind)(HN=C(Me)ind)$, and cesium is a unit dosage form.

Still further encompassed by the invention are pharmaceutical packs and/or kits comprising compositions described herein, or a unit dosage form comprising a provided composition, and a container (e.g., a foil or plastic package, or other suitable container). Optionally instructions for use are additionally provided in such kits.

In some embodiments, the present invention can be provided as a unit dosage form. Indeed, a vial comprising sodium trans-[tetrachlorobis(1H-indazole)ruthenate (III)], mannitol, citric acid, sodium citrate is a unit dosage form depicted in Table 3

TABLE 3

Pharmaceutical Components

| Component | Function | Weight % | Amount/vial |
|---|---|---|---|
| sodium trans-[tetrachlorobis(1H-indazole)ruthenate (III)] | Active | 47.5 | 100 mg |
| Mannitol | Cryoprotectant | 47.5 | 100 mg |
| Citric Acid | Buffer component | 3.37 | 7.1 mg |
| Sodium citrate | Buffer component | 1.63 | 3.4 mg |

In some embodiments, the pharmaceutical components described in Table 3 further comprise cesium;
wherein:
cesium is not more than 0.25 weight percentage of the composition.

In some embodiments, the pharmaceutical components described in Table 3 further comprise cesium, $Ru^{III}Cl_3(Hind)_2(H_2O)$, $Ru^{III}Cl_3(Hind)_2(CH_3CN)$, and
$Ru^{III}Cl_3(Hind)(HN=C(Me)ind)$;

wherein:

cesium is not more than about 0.25 weight percentage of the composition, $Ru^{III}Cl_3(Hind)_2(H_2O)$ is not more than about 0.5 weight percentage of the composition, $Ru^{III}Cl_3(Hind)_2(CH_3CN)$ is not more than about 1.25 weight percentage of the composition, and $Ru^{III}Cl_3(Hind)(HN=C(Me)ind)$ is not more than about 1.0 weight percentage of the composition.

In some embodiments, the pharmaceutical composition is selected from those in

TABLE 4

Pharmaceutical Component Ranges

| Component | Function | Weight % Range | Amount/vial |
|---|---|---|---|
| sodium trans-[tetrachlorobis(1H-indazole)ruthenate (III)] | Active | 42.75-52.25 | 90-110 mg |
| Mannitol | Cryoprotectant | 42.75-52.25 | 90-110 mg |
| Citric Acid | Buffer component | 3.033-3.707 | 6.39-7.81 mg |
| Sodium citrate | Buffer component | 1.467-1.793 | 3.06-3.74 mg |

In some embodiments, the pharmaceutical components described in Table 4 further comprise cesium;

wherein:

cesium is not more than 0.25 weight percentage of the composition.

In some embodiments, the pharmaceutical components described in Table 4 further comprise cesium, $Ru^{III}Cl_3(Hind)_2(H_2O)$, $Ru^{III}Cl_3(Hind)_2(CH_3CN)$, and $Ru^{III}Cl_3(Hind)(HN=C(Me)ind)$;

wherein:

cesium is not more than about 0.25 weight percentage of the composition, $Ru^{III}Cl_3(Hind)_2(H_2O)$ is not more than about 0.5 weight percentage of the composition, $Ru^{III}Cl_3(Hind)_2(CH_3CN)$ is not more than about 1.25 weight percentage of the composition, and $Ru^{III}Cl_3(Hind)(HN=C(Me)ind)$ is not more than about 1.0 weight percentage of the composition.

In some embodiments, the present invention can be provided as a unit dosage form. Indeed, a vial comprising sodium trans-[tetrachlorobis(1H-indazole)ruthenate (III)], mannitol, citric acid, sodium citrate is a unit dosage form depicted in Table 5:

TABLE 5

Pharmaceutical Components

| Component | Function | Weight % | Amount/vial |
|---|---|---|---|
| sodium trans-[tetrachlorobis(1H-indazole)ruthenate (III)] | Active | 49.86 | 300 mg |
| Mannitol | Cryoprotectant | 49.86 | 300 mg |
| Citric Acid | Buffer component | 0.188 | 1.13 mg |
| Sodium citrate | Buffer component | 0.092 | 0.55 mg |

In some embodiments, the pharmaceutical components described in Table 5 further comprise cesium;

wherein:

cesium is not more than 0.25 weight percentage of the composition.

In some embodiments, the pharmaceutical components described in Table 5 further comprise cesium, $Ru^{III}Cl_3(Hind)_2(H_2O)$, $Ru^{III}Cl_3(Hind)_2(CH_3CN)$, and $Ru^{III}Cl_3(Hind)(HN=C(Me)ind)$;

wherein:

cesium is not more than about 0.25 weight percentage of the composition, $Ru^{III}Cl_3(Hind)_2(H_2O)$ is not more than about 0.5 weight percentage of the composition, $Ru^{III}Cl_3(Hind)_2(CH_3CN)$ is not more than about 1.25 weight percentage of the composition, and $Ru^{III}Cl_3(Hind)(HN=C(Me)ind)$ is not more than about 1.0 weight percentage of the composition.

In some embodiments, the pharmaceutical composition is selected from those in

TABLE 6

Pharmaceutical Components

| Component | Function | Weight % Range | Amount/vial |
|---|---|---|---|
| sodium trans-[tetrachlorobis(1H-indazole)ruthenate (III)] | Active | 44.87-54.85 | 270-330 mg |
| Mannitol | Cryoprotectant | 44.87-54.85 | 270-330 mg |
| Citric Acid | Buffer component | 0.169-0.207 | 1.02-1.24 mg |
| Sodium citrate | Buffer component | 0.0828-0.1012 | 0.495-0.605 mg |

In some embodiments, the pharmaceutical components described in Table 6 further comprise cesium;

wherein:

cesium is not more than about 0.25 weight percentage of the composition.

In some embodiments, the pharmaceutical components described in Table 6 further comprise cesium, $Ru^{III}Cl_3(Hind)_2(H_2O)$, $Ru^{III}Cl_3(Hind)_2(CH_3CN)$, and $Ru^{III}Cl_3(Hind)(HN=C(Me)ind)$;

wherein:

cesium is not more than about 0.25 weight percentage of the composition, $Ru^{III}Cl_3(Hind)_2(H_2O)$ is not more than about 0.5 weight percentage of the composition, $Ru^{III}Cl_3(Hind)_2(CH_3CN)$ is not more than about 1.25 weight percentage of the composition, and $Ru^{III}Cl_3(Hind)(HN=C(Me)ind)$ is not more than about 1.0 weight percentage of the composition.

In some embodiments, the pharmaceutical components are as described in any of Tables 3-6, and further comprise cesium. In some embodiments, cesium is present in an amount of about 0.001, 0.002, 0.003, 0.004, 0.005, 0.006, 0.007, 0.008, 0.009, 0.010, 0.015, 0.020, 0.025, 0.030, 0.035, 0.040, 0.045, 0.050, 0.055, 0.060, 0.065, 0.070, 0.075, 0.080, 0.085, 0.090, 0.095, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, or 1.0 weight percentage of the composition.

3.4 Methods of Treatment

In some embodiments, the present invention provides a method for treating cancer in a subject in need thereof comprising administering to the subject a provided composition of IT-139 described above and herein. In some such embodiments, the subject is a human patient.

In some embodiments, the present invention provides a method for treating cancer in a subject in need thereof comprising administering a provided composition of IT-139 described above and herein in combination with a chemotherapeutic agent.

In some embodiments, the present invention provides a method for treating cancer in a subject in need thereof comprising administering a provided composition of IT-139 described above and herein in combination with an immuno-oncology agent.

According to another embodiment, the present invention relates to a method of treating a cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia, comprising administering IT-139, or a pharmaceutically acceptable composition thereof, According to another embodiment, the present invention relates to a method of treating a cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia, comprising administering IT-139, or a pharmaceutically acceptable composition thereof, in combination with a chemotherapeutic agent.

According to another embodiment, the present invention relates to a method of treating a cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia, comprising administering IT-139, or a pharmaceutically acceptable composition thereof, in combination with an immuno-oncology agent.

Another embodiment provides a method for treating cancer by reducing the amount of GRP78 in cancer cells following administration of IT-139.

According to another embodiment, the present invention provides a method for treating cancer by reducing the amount of GRP78 in cancer cells following administration of IT-139 in combination with a chemotherapy agent, wherein the administration of IT-139, or a pharmaceutically acceptable composition thereof, results in a reduction in the amount of GRP78 as compared to administration of the chemotherapy agent.

According to another embodiment, the present invention provides a method for treating cancer by reducing the amount of GRP78 in cancer cells following administration of IT-139 in combination with an immune-oncology agent, wherein the administration of IT-139, or a pharmaceutically acceptable composition thereof, results in a reduction in the amount of GRP78 as compared to administration of the immune-oncology agent alone.

The order of administration of therapeutics should be carefully considered. Without wishing to be bound to any particular theory, the mechanism of action and down-regulation of GRP78 dictates that any chemotherapeutic agent should be administered first, followed by IT-139 for maximum therapeutic benefit. As stated above, treatment with a range of chemotherapeutic agents results in an increase ER stress, which induces production of GRP78. This process is a cellular survival mechanism. Administration of IT-139 decreases the level of stress-induced GRP78, which removes a cellular survival pathway. The ultimate result is increased cancer cell death and increased anti-tumor effect.

According to one embodiment of the present invention provides a method for treating cancer in a patient in need thereof, comprising the steps of:
 1) administering to the patient a chemotherapy agent;
 2) subsequently administering IT-139, or a pharmaceutically acceptable composition thereof; to the patient; and
 3) optionally repeating steps 1 and 2.

In certain embodiments, the IT-139, or a pharmaceutically acceptable composition thereof, is administered 1 day after the chemotherapy agent. In other embodiments, IT-139, or a pharmaceutically acceptable composition thereof, is administered to the patient 1 week after the chemotherapy agent. In yet other embodiments, IT-139 is administered to a patient between 1 and seven days after the chemotherapy agent.

In certain embodiments, the IT-139, or a pharmaceutically acceptable composition thereof, is administered simultaneously with the chemotherapy agent. In certain embodiments, the IT-139, or a pharmaceutically acceptable composition thereof, and the chemotherapy agent are administered within about 20-28 hours of each other, or within about 22-26 hours of each other, or within about 24 hours of each other.

In certain embodiments, the IT-139, or a pharmaceutically acceptable composition thereof, is administered before the chemotherapy agent. In certain embodiments, the IT-139, or a pharmaceutically acceptable composition thereof, is administered at least about 8-16 hours before the chemotherapy agent, or at least about 10-14 hours before the chemotherapy agent, or at least about 12 hours before the chemotherapy agent.

In certain embodiments, the IT-139, or a pharmaceutically acceptable composition thereof, is administered at least about 20-28 hours before the chemotherapy agent, or at least about 22-26 hours before the chemotherapy agent, or at least about 24 hours before the chemotherapy agent.

In certain embodiments, the IT-139, or a pharmaceutically acceptable composition thereof, is administered at least about 44-52 hours before the chemotherapy agent, or at least about 46-50 hours before the chemotherapy agent, or at least about 48 hours before the chemotherapy agent.

In certain embodiments, the IT-139, or a pharmaceutically acceptable composition thereof, is administered at least about 64-80 hours before the chemotherapy agent, or at least about 70-74 hours before the chemotherapy agent, or at least about 72 hours before the chemotherapy agent.

In certain embodiments, the IT-139, or a pharmaceutically acceptable composition thereof, is administered before the chemotherapy agent. In certain embodiments, the IT-139, or a pharmaceutically acceptable composition thereof, is administered at least about 8-16 hours after the chemotherapy agent, or at least about 10-14 hours after the chemotherapy agent, or at least about 12 hours after the chemotherapy agent.

In certain embodiments, the IT-139, or a pharmaceutically acceptable composition thereof, is administered at least about 20-28 hours after the chemotherapy agent, or at least about 22-26 hours after the chemotherapy agent, or at least about 24 hours after the chemotherapy agent.

In certain embodiments, the IT-139, or a pharmaceutically acceptable composition thereof, is administered at least about 44-52 hours after the chemotherapy agent, or at least about 46-50 hours after the chemotherapy agent, or at least about 48 hours after the chemotherapy agent.

In certain embodiments, the IT-139, or a pharmaceutically acceptable composition thereof, is administered at least about 64-80 hours after the chemotherapy agent, or at least about 70-74 hours after the chemotherapy agent, or at least about 72 hours after the chemotherapy agent.

In certain embodiments, the chemotherapeutic agent is selected from the group consisting of gemcitabine, nanoparticle albumin paclitaxel, paclitaxel, docetaxel, cabazitaxel, oxaliplatin, cisplatin, carboplatin, doxorubicin, daunorubicin, sorafenib, everolimus and vemurafenib. In certain embodiments, the chemotherapeutic agent is gemcitabine.

According to one embodiment of the present invention provides a method for treating pancreatic cancer in a patient in need thereof, comprising the steps of:
1) administering a gemcitabine and albumin nanoparticle paclitaxel;
2) subsequently administering IT-139, or a pharmaceutically acceptable composition thereof; and
3) optionally repeating steps 1 and 2.

In certain embodiments, the IT-139, or a pharmaceutically acceptable composition thereof, is administered simultaneously with gemcitabine. In certain embodiments, the IT-139, or a pharmaceutically acceptable composition thereof, and gemcitabine are administered within about 20-28 hours of each other, or within about 22-26 hours of each other, or within about 24 hours of each other.

In certain embodiments, the IT-139, or a pharmaceutically acceptable composition thereof, is administered before gemcitabine. In certain embodiments, the IT-139, or a pharmaceutically acceptable composition thereof, is administered at least about 8-16 hours before gemcitabine, or at least about 10-14 hours before gemcitabine, or at least about 12 hours before gemcitabine.

In certain embodiments, the IT-139, or a pharmaceutically acceptable composition thereof, is administered at least about 20-28 hours before gemcitabine, or at least about 22-26 hours before gemcitabine, or at least about 24 hours before gemcitabine.

In certain embodiments, the IT-139, or a pharmaceutically acceptable composition thereof, is administered at least about 44-52 hours before gemcitabine, or at least about 46-50 hours before gemcitabine, or at least about 48 hours before gemcitabine.

According to one embodiment of the present invention provides a method for treating cancer in a patient in need thereof, comprising administering IT-139, or a pharmaceutically acceptable composition thereof, in combination with an immuno-oncology agent. In certain embodiments, the immune-oncology agent is administered to the patient prior to the administration of IT-139, or a pharmaceutically acceptable composition thereof.

In certain embodiments, the IT-139, or a pharmaceutically acceptable composition thereof, is administered simultaneously with the immuno-oncology agent. In certain embodiments, the IT-139, or a pharmaceutically acceptable composition thereof, and the immuno-oncology agent are administered within about 20-28 hours of each other, or within about 22-26 hours of each other, or within about 24 hours of each other.

In certain embodiments, the IT-139, or a pharmaceutically acceptable composition thereof, is administered before the immuno-oncology agent. In certain embodiments, the IT-139, or a pharmaceutically acceptable composition thereof, is administered at least about 8-16 hours before the immuno-oncology agent, or at least about 10-14 hours before the immuno-oncology agent, or at least about 12 hours before the immuno-oncology agent.

In certain embodiments, the IT-139, or a pharmaceutically acceptable composition thereof, is administered at least about 20-28 hours before the immuno-oncology agent, or at least about 22-26 hours before the immuno-oncology agent, or at least about 24 hours before the immuno-oncology agent.

In certain embodiments, the IT-139, or a pharmaceutically acceptable composition thereof, is administered at least about 44-52 hours before the immuno-oncology agent, or at least about 46-50 hours before the immuno-oncology agent, or at least about 48 hours before the immuno-oncology agent.

In certain embodiments, the IT-139, or a pharmaceutically acceptable composition thereof, is administered at least about 64-80 hours before the immuno-oncology agent, or at least about 70-74 hours before the immuno-oncology agent, or at least about 72 hours before the immuno-oncology agent.

In certain embodiments, the IT-139, or a pharmaceutically acceptable composition thereof, is administered after the immuno-oncology agent. In certain embodiments, the IT-139, or a pharmaceutically acceptable composition thereof, is administered at least about 8-16 hours after the immuno-oncology agent, or at least about 10-14 hours after the immuno-oncology agent, or at least about 12 hours after the immuno-oncology agent.

In certain embodiments, the IT-139, or a pharmaceutically acceptable composition thereof, is administered at least about 20-28 hours after the immuno-oncology agent, or at least about 22-26 hours after the immuno-oncology agent, or at least about 24 hours after the immuno-oncology agent.

In certain embodiments, the IT-139, or a pharmaceutically acceptable composition thereof, is administered at least about 44-52 hours after the immuno-oncology agent, or at least about 46-50 hours after the immuno-oncology agent, or at least about 48 hours after the immuno-oncology agent.

In certain embodiments, the IT-139, or a pharmaceutically acceptable composition thereof, is administered at least about 64-80 hours after the immuno-oncology agent, or at least about 70-74 hours after the immuno-oncology agent, or at least about 72 hours after the immuno-oncology agent.

In certain embodiments, the immune-oncology agent is selected from the group consisting of cytokines, checkpoint inhibitors and antibodies other than PD-1 antibodies. In certain embodiments, the immune-oncology agent is selected from the group consisting of interferon, interleukin, PD-L1 antibodies, alemtuzumab, ipilimumab, ofatumumab, atezolizumab and rituximab.

According to one embodiment of the present invention provides a method for treating cancer in a patient in need thereof, comprising administering IT-139, or a pharmaceutically acceptable composition thereof, in combination with a PD-1 antibody. In certain embodiments, the PD-1 antibody is administered prior to the administration of the IT-139, or a pharmaceutically acceptable formulation thereof.

According to one embodiment of the present invention provides a method for treating cancer in a patient in need thereof, comprising administering IT-139, or a pharmaceutically acceptable composition thereof, in combination with a PD-L1 antibody. In certain embodiments, the PD-L1 antibody is administered prior to the administration of the IT-139, or a pharmaceutically acceptable formulation thereof.

According to one embodiment of the present invention provides a method for treating cancer in a patient in need thereof, comprising administering IT-139, or a pharmaceutically acceptable composition thereof, in combination with an immune-oncology agent other than a PD-1 antibody. In certain embodiments, the immune-oncology agent other than a PD-1 antibody is administered prior to the administration of the IT-139, or a pharmaceutically acceptable formulation thereof.

EXEMPLIFICATION

In order that the invention described herein may be more fully understood, the following examples are set forth. It will be understood that these examples are for illustrative purposes only and are not to be construed as limiting this invention in any manner.

Analytical Methods

The following analytical methods were utilized to characterize the compounds of the present invention.

HPLC Method 1 Assay and identity of sodium trans-[tetrachlorobis(1H-indazole) ruthenate (III)] was determined by high pressure liquid chromatography with UV detection at 292 nm. IT-139 drug product was dissolved in water at concentration of 1 mg/mL, and 10 µL was injected onto an Agilent Zorbax SB-C18 (3 µm, 4.6×150 mm) HPLC column. Mobile phase A consisted of 0.1% trifluoroacetic acid in water and mobile phase B consisted of 0.1% trifluoroacetic acid in acetonitrile. Separation was achieved by gradient flow at 1.0 mL/minute such that mobile phase A constituting from 90% to 10% from time zero to 12 minutes, with mobile phase B constituting from 10% to 90% over 12 minutes. The gradient was then reversed from 10% mobile phase A and 90% mobile phase B to 90% A and 10% B from 12 minutes to 13 minutes. This continued until the end of the run at 15 minutes. The analyte retention time was 7.7 minutes. Sample temperature was maintained at 5° C., and column temperature was maintained at 25° C.

HPLC Method 2 Two HPLC methods are used because two different impurities co-elute using HPLC Method 1. Related substances for IT-139 drug product were determined by high pressure liquid chromatography with UV detection at 292 nm. IT-139 drug product was dissolved in water at concentration of 1 mg/mL, and 10 µL was injected onto an Agilent Zorbax SB-C18 (3 µm, 4.6×150 mm) HPLC column. Mobile phase A consisted of 0.1% trifluoroacetic acid in water and mobile phase B consisted of 0.1% trifluoroacetic acid in acetonitrile. Separation was achieved by gradient flow at 1.0 mL/minute such that mobile phase A constituted from 90% to 10% from time zero to 15 minutes, with mobile phase B constituted from 10% to 90% over 15 minutes. The gradient was held at 10% A and 90% B from 15 minutes to 19.9 minutes. The gradient was then reversed to 90% A and 10% B from 19.9 minutes to 20 minutes, and was held until the end of the run at 26 minutes. Sample temperature was maintained at 5° C., and column temperature was maintained at 25° C.

HPLC Method 3 Analysis which does not resolve Formula I-b from Compound A, Compound B, and Compound C uses high pressure liquid chromatography with UV detection at 297 nm. IT-139 drug substance was dissolved in water at a concentration of 0.5 mg/mL, and 10 µL was injected onto a Phenomenex Luna, Phenyl-Hexyl (150×3 mm×3 µm) HPLC column. Mobile phase consisted of 25% (volume/volume) methanol in 20 mM ammonium acetate buffer with 4 mM acetic acid. Separation was achieved by isocratic flow at 1.0 mL/min for a total run time of 27 mins with the column temperature maintained at 25° C.

Elemental Analysis Galbraith Laboratories (Knoxville, TN) performed all elemental analysis measurements. Carbon, hydrogen, and nitrogen analysis was performed using standard operating procedure ME-14, which requires 1-5 mg weighed into a tin capsule followed by combustion at 920-980° C. in a PerkinElmer 2400 Series II CHNS/O Analyzer. Sodium and ruthenium analysis performed by inductively coupled plasma atomic emission spectrometery using standard operating procedure ME-70 and ICP-OES Optima 5300 instrument. Cesium analysis was performed by inductively coupled plasma atomic emission spectrometery using standard operating procedure ME-30.

X-Ray Diffraction X-ray data was collected on a Bruker D8 Venture Single Crystal Diffractometer with PHOTON 100 CMOS Detector, IpS Copper MX source and Oxford Cryostream Plus low temperature device or a Bruker Smart Apex2 Single Crystal Diffractometer with Copper radiation with room temperature data collection.

Example 1—Purification of Ruthenium Chloride $RuCl_{3-x}H_2O$ (100.0 g) was combined with conc. HCl 600 mL and ethanol 99% 600 mL. The mixture was distilled under air at normal pressure, to reduce the mixture volume below 400 mL. The resulting concentrated ruthenium chloride solution remaining in the distillation flask was then cooled to ambient temperature, filtered through a medium porosity glass Buchner funnel, the Buchner funnel and the flask were rinsed with conc. HCl and the combined filtrates were diluted with additional conc. HCl up to about 500 mL total volume.

Example 2—Preparation of the Indazolium Salt

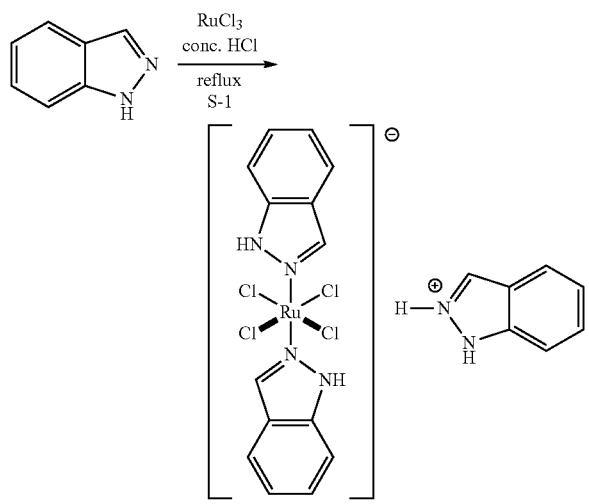

1H-Indazole 300.0 g (2.54 mol; 6.64 eq.) was combined with water (800 mL). Concentrated HCl (4 L) was added, the mixture was stirred until dissolved (20 min). This indazole solution was charged into a 15 L jacketed stirred glass and Teflon reactor, with a large efficient paddle-shaped stirrer, internal thermo-probe, air-cooled reflux condenser topped with a gas outlet tube (for HCl gas release) and 0.5 L-sized addition funnel with a stem extended with polyethylene tubing. Additional conc. HCl 4.0 L was combined with the indazole solution in the reactor, and the mixture was stirred and heated until the internal temperature reached 90° C., the stirring speed was then turned up, to 250 rpm, and the temperature was maintained at 90° C. for at least 30 min. The solution of RuCl$_3$ from Example 1 was then carefully added dropwise over a period of about 5 hours, from the funnel with stem extended by polyethylene tubing, while maintaining rapid stirring at 250 rpm. After complete addition, the addition funnel was rinsed down with a small amount of concentrated HCl (2×50 mL) and the rinses were also added to the reactor. The combined volume of reaction mixture was 9.5 L; the product precipitated in the form of tan microcrystalline flakes. After the complete addition, the reaction was stirred at 250 rpm at 90° C. for additional 10 hours. The reaction mixture was cooled to 25° C. with stirring, transferred through the bottom drain valve into a polyethylene plastic bucket. The precipitated product was collected by filtration on 3 L medium porosity glass filter funnel. The reactor and the stirring paddle was washed down with 2 M HCl, the washings were added to the material on the filter funnel. The obtained solids were thoroughly rinsed with additional 2 M HCl, about 2 L, and then partially dried by suction overnight. This provided 598 g of crude indazolium salt, wet with residual 2M HCl, as a brown sticky solid. HPLC analysis: Method 1: 97.7%, Method 2: 98.0%.

Example 3—Preparation of the Cesium Salt

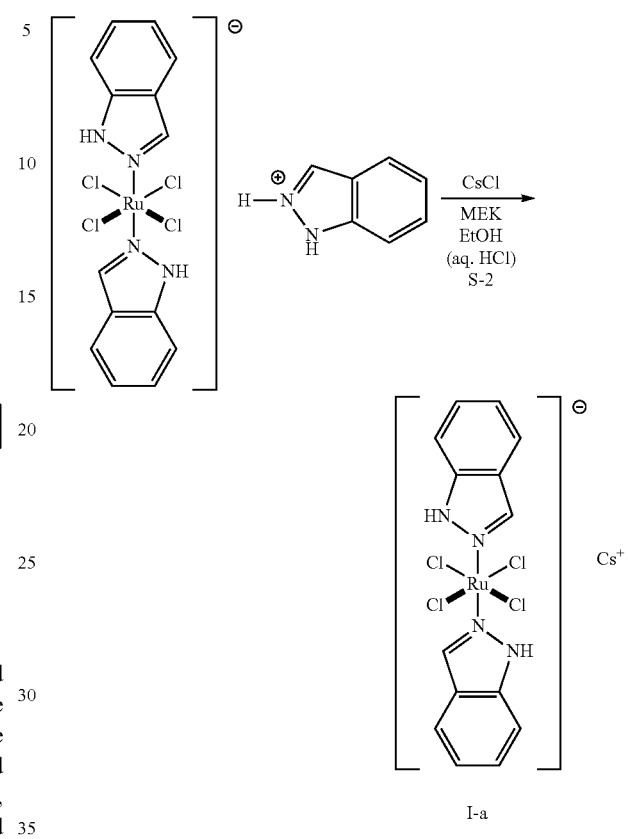

A 10 L wide-mouth flask was charged with wet indazolium salt from Example 2 and solid powdered CsCl 180.0 g (1.07 mol; 2.8 eq.) was added. Pure non-denatured ethanol 99% (1.8 L) was combined with MEK (2.0 L) was combined with the indazolium salt and CsCl mixture in a 10 L flask. The mixture was mechanically stirred using a wide Teflon paddle, at 22° C. At first for 5 min at 200 rpm followed by high speed stirring for 2 hours at 700 rpm. The resulting orange slurry was collected by filtration using a medium porosity glass Buchner funnel (3 L), the solids were washed with 99% ethanol thoroughly and the filter cake material was partially dried by suction, for about 1 hour. The obtained material, containing the cesium salt in the form of an orange-colored MEK solvate intermixed with leftover CsCl, was transferred into a large 4 L beaker. One liter of a mixture of 2:1 (v/v) ethanol with water was added to the crude Cs salt solid in a beaker. The slurry was stirred mechanically at 350 rpm for 15 minutes in open beaker: during this time the bright orange color of MEK solvate slurry turned into a cinnamon red-brown color of hydrate. The solids were collected by filtration using the same Buchner funnel used previously to filter the Cs salt. The obtained solids were washed thoroughly with 99% ethanol, about 1 liter. The material was dried by suction and then in vacuo for 14 hours (overnight). Yield was 226.90 g (0.350 mol) of a cinnamon red-brown solid, HPLC analysis: no free indazole detected, Method 1: 98.6%, Method 2: 99.0% pure. Elemental analysis results found: Cs: 21.6%, Ru: 16.6%, Cl: 21.96%. Theoretical values for dihydrate: Cs: 20.5%, Ru: 15.6%, Cl: 21.88%. Theoretical values for monohydrate: Cs: 21.1%, Ru: 16.0%, Cl: 22.51%. X-ray diffraction analysis of a single crystal from a vacuum-dried sample indicated about 50% occupancy density of the two hydrate water molecules in the crystal structure.

Example 4—Preparation of the Sodium Salt

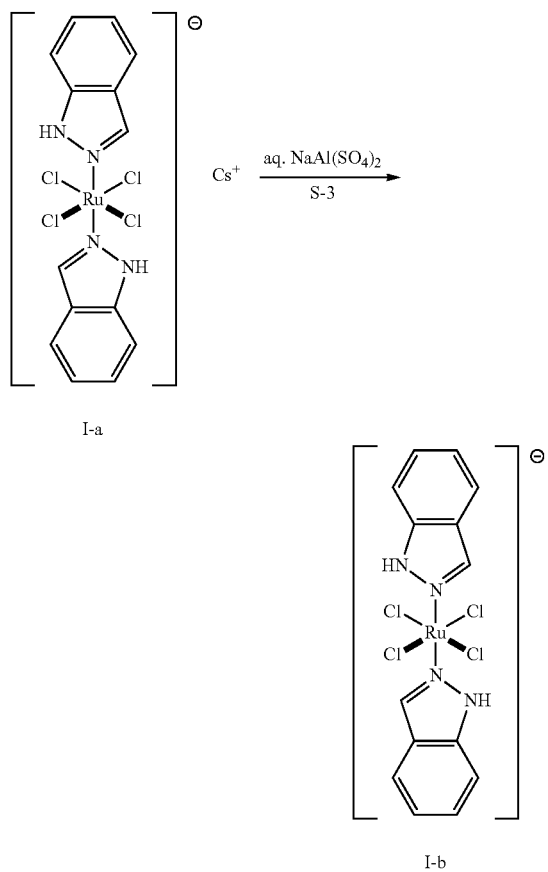

I-a

I-b

Solid Al$_2$(SO$_4$)$_3$·18H$_2$O 1000 g (3.0 mol of Al) was gradually added into stirred D.I. water (2.0 L), followed by solid Na$_2$SO$_4$ 213.0 g (3.0 mol of Na). The mixture was stirred to complete dissolution (about 30 min), the total solution volume was adjusted to 2.7 L volume by addition of D.I. water. The resulting 1.1 M solution was filtered before use through a fine 0.45 micron SteriCup Durapore membrane, to obtain 2.7 L of 1.1M solution of NaAl(SO$_4$)$_2$. This 1.1M NaAl(SO$_4$)$_2$ solution was combined with 226.9 g of the Cs salt (0.350 mol) from Example 5, in a 4 L beaker. Solid powdered CsCl 6.0 g was added to the mix, to seed the formation of Cs alum. The mixture was stirred magnetically with a large Teflon-coated rod stirbar for 30 hours at ambient temperature. During this time, the red-brown slurry of the cesium salt turned into coffee-brown black slurry of IT-139 intermixed with fine white salt-like crystals of cesium aluminum salts. The solids were collected by filtration, using a medium porosity Buchner (3 L), the reaction flask and the solids were thoroughly washed with saturated (=1.5M) aqueous Na$_2$SO$_4$, about 1.5 L total (in three portions, 3×0.5 L, until the filtrates were colorless), and the solids were dried by suction on Buchner funnel, followed by drying in vacuo for at least 1 day. The thoroughly dried solids were transferred into a 2 L wide mouth Erlenmeyer flask with 700 mL acetonitrile. The mixture was stirred mechanically for 15 min. The resulting orange slurry was filtered, the insoluble sulfate salts were removed from the mixture on a medium porosity Buchner funnel. The salt cake was rinsed with additional acetonitrile 300 mL (3×100 mL, until colorless) and then discarded. The combined orange filtrates in a 5 L round flask were diluted with 4 L of MTBE (added in four 1 L portions, with gentle stirring), the flask was set aside for 30 min to complete the precipitation. The precipitated crude Na salt was collected by filtration, rinsed thoroughly with MTBE (2×0.5 L) and then dried by suction and in vacuo. The yield was 190.4 g (100% of theory, calculated as the dihydrate) of a crude product as fluffy brown solid, retaining MTBE in the form of solvate, HPLC purity 98.4% by Method 1. Elemental analysis demonstrates that this product contains 0.1-0.8 wt % cesium. The structure of the product was confirmed by x-ray diffraction.

Example 5—Removal of Residual Cesium 190.4 g of material from Example 4 was transferred into a dry 10 L flask. Equal weight of activated 4 A molecular sieves powder (191 g), was added. [Aldrich 688363-1KG, sodium aluminosilicate, "SYLOSIV A4" manufactured by Grace Davidson]. Methyl ethyl ketone (4.2 L) was added to the flask and the mixture was stirred mechanically. Methanol (600 mL) was gradually added into the stirred slurry over a 5 min period. The stirring (800 rpm) was continued for 30 min, at this time nearly all dark brown lumps of material was dissolved. The resulting orange slurry was filtered through Whatman fiberglass GF-B filter disc placed on top of a fine-porosity glass Buchner porosity funnels. The spent molecular sieves were rinsed with additional MEK 0.4 L (2×200 mL) and discarded. The combined filtrates were precipitated by gradual addition of MTBE 10 L with mechanical stirring. The stirring was turned off and the mixture was set aside to precipitate for 30 minutes. The precipitated product was collected by filtration (3 L Buchner funnel), rinsed thoroughly with MTBE 1 L (2×0.5 L) and dried by suction, for about 2 hours, until the Buchner funnel was no longer cold. This provided 184 g of purified sodium salt. To remove the solvent traces, the purified material was treated with wet MTBE. 184 g of the purified sodium salt was combined with 3.3 L of wet MTBE (water saturated MTBE), in a 5 L wide mouth Erlenmeyer and mechanically stirred (200 rpm) for 40 min. The resulting brown solids were collected by filtration. The solids were rinsed with wet MTBE, dried by suction and then thoroughly dried in vacuo overnight (15 hours). The yield was 176.11 g of a coffee-brown granular heavy solid, 98.7% pure by HPLC. (Method 1) This corresponds to 85% overall yield from RuCl$_{3-x}$H$_2$O (beginning with Example 1). Elemental analysis determined that there was 35 to 750 ppm of cesium remaining.

Example 6—Solution Stability Studies

Figure 2:
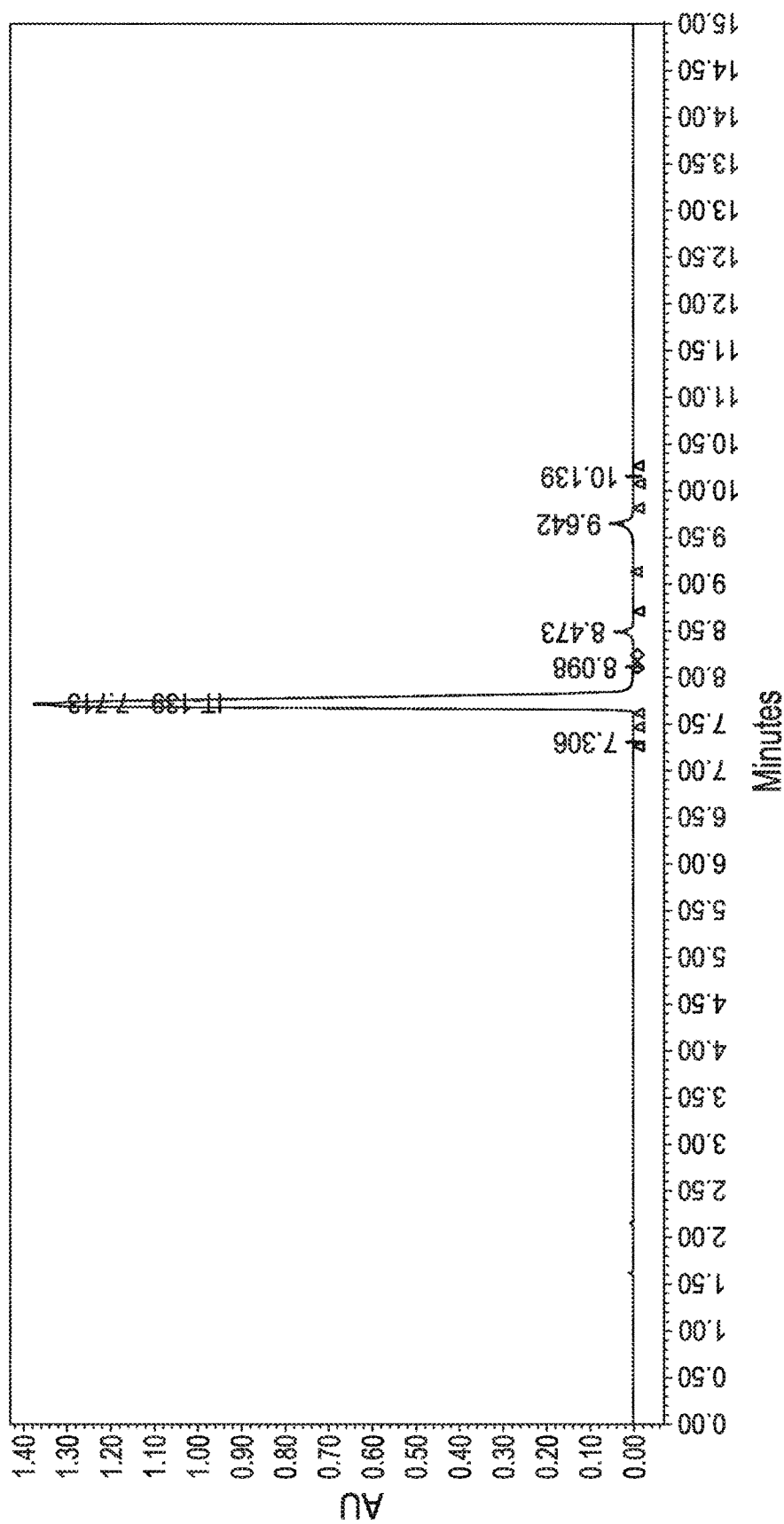
FIG. 2. HPLC chromatogram for IT-139 stored refrigerated (2-8° C.) for 18 hours FIG. 3. HPLC chromatogram for IT-139 stored at room temperature (18-22° C.) for 18 hours FIG. 4. HPLC chromatogram using HPLC Method #3 of Formula I-b prepared using previous synthetic methodology disclosed in U.S. Pat. No. 8,362,266.
Figure 3:
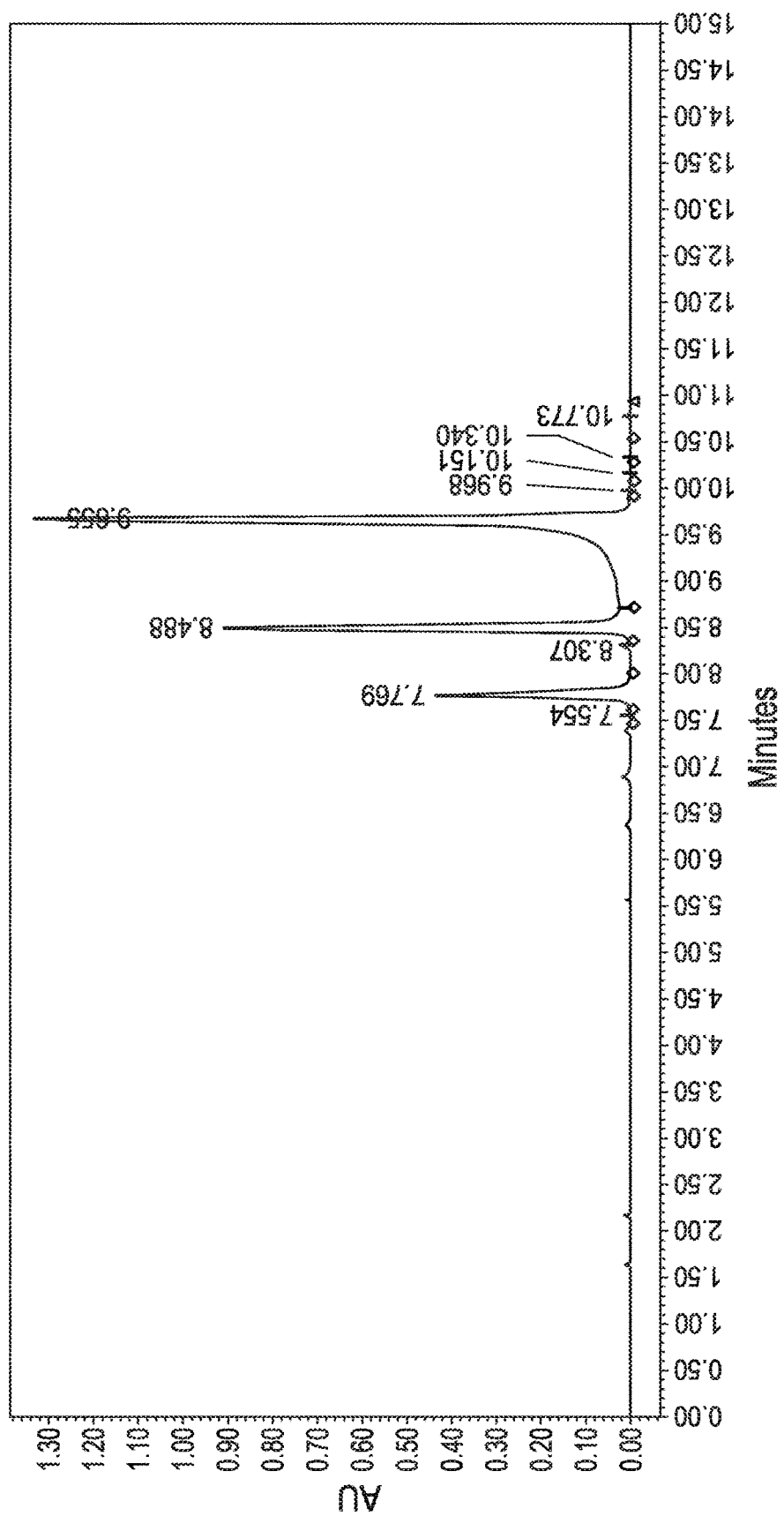

Compound from Example 5 was prepared at room temperature (20° C.) using room temperature solutions, and refrigerated (2-8° C.) using cold (2-8° C.) solutions, for a total volume of 500 mL for each. Citric acid solution was prepared by dissolving 19.2 grams of citric acid in 1 L of water. Sodium citrate solution was prepared by dissolving 29.4 grams of sodium citrate in 1 L of water. Sodium citrate solution was added to the citric acid solution until the pH was increased from 2.0 to 3.4. Mannitol solution was prepared by dissolving 13.3 g in 200 mL of water. Solutions of Formula I-b were prepared by adding 16.6 mL of citrate buffer to 400 mL water. 3.33 g sodium trans[tetrachlorobis (1H-indazole)ruthenate(III)] was added to the solution and stirred for 10 minutes. 50 mL of mannitol solution was added followed by 33.4 mL of water for a final volume of 500 mL IT-139 bulk solution. The room temperature (18-22° C.) sample was stirred using a magnetic stir plate on the laboratory bench, and the refrigerated sample was stirred using a magnetic stir plate in a refrigerator (2-8° C.). Aliquots of 100 µL were taken from each sample immediately upon dissolution (T=0) and at time points of 0.5, 1, 2, 3, 4, 5, 6, 18, 24, 32, and 48 hours. Each sample was added to 1.9 mL methanol in an HPLC vial and mixed by vortex. The purity of sodium trans[tetrachlorobis(1H-indazole)ruthenate(III)] in the bulk solution stored at room temperature (18-22° C.) decreased from 96.8% to 12.1% after 18 hours. The purity of sodium trans[tetrachlorobis(1H-indazole)ruthenate(III)] in the bulk solution stored refrigerated (2-8° C.) decreased from 97.05% to 95.4% after 18 hours, and to 89.8% after 48 hours. FIG. 1 demonstrates the percentage of sodium trans[tetrachlorobis(1H-indazole)ruthenate(III)] at room temperature (18-22° C.) over 18 hours and refrigerated (2-8° C.) over 48 hours. Table 7 shows the percentage of sodium trans[tetrachlorobis(1H-indazole)ruthenate(III)](RT 7.7 min) and impurities (RRT 0.7, 1.9, and total of unspecified RRT) for each sample based on HPLC peak area. HPLC chromatograms for IT-139 samples stored refrigerated or at room temperature at the 18 hour time point are shown in FIG. 2 and FIG. 3, respectively.

TABLE 7

HPLC analysis of sodium trans[tetrachlorobis(1H-indazole)ruthenate(III)] stored at 20° C. and at 4° C. analyzed over time.

| Sample Temp. | Time (h) | % Peak Area RT 7.7 min | % Peak Area RRT 1.09 | % Peak Area RRT 1.28 | % Peak Area Unspecified |
|---|---|---|---|---|---|
| 20° C. | 0 | 96.8 | 0.88 | 2.26 | <0.1 |
| 20° C. | 0.5 | 96.8 | 1.08 | 2.07 | <0.1 |
| 20° C. | 1 | 96.5 | 1.14 | 2.28 | <0.1 |
| 20° C. | 2 | 96.3 | 1.22 | 2.34 | 0.13 |
| 20° C. | 3 | 95.9 | 1.35 | 2.55 | 0.16 |
| 20° C. | 4 | 95.4 | 1.47 | 2.89 | 0.25 |
| 20° C. | 5 | 94.9 | 1.58 | 3.27 | 0.26 |
| 20° C. | 6 | 94.0 | 1.88 | 4 | 0.13 |
| 20° C. | 18 | 12.1 | 25.2 | 60.87 | 1.82 |
| 4° C. | 0 | 97.1 | 0.96 | 1.91 | <0.1 |
| 4° C. | 0.5 | 97.3 | 0.96 | 1.7 | <0.1 |
| 4° C. | 1 | 97.0 | 1.03 | 1.9 | <0.1 |
| 4° C. | 2 | 97.0 | 1.04 | 1.86 | 0.14 |
| 4° C. | 3 | 96.8 | 1.07 | 0.94 | 0.16 |
| 4° C. | 4 | 96.5 | 1.13 | 2.14 | 0.26 |
| 4° C. | 5 | 96.6 | 1.11 | 2.2 | <0.1 |
| 4° C. | 6 | 96.8 | 1.09 | 2.07 | <0.1 |
| 4° C. | 18 | 95.4 | 1.45 | 3.07 | 0.11 |
| 4° C. | 24 | 94.8 | 1.34 | 3.76 | <0.1 |
| 4° C. | 32 | 94.9 | 1.33 | 3.65 | <0.1 |
| 4° C. | 48 | 89.8 | 2.39 | 7.56 | <0.1 |

Example 7—Preparation of Compound A

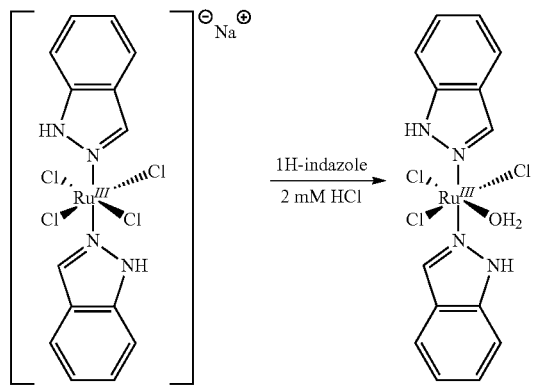

Indazole (400 mg, 3.40 mmol, 1 eq.) was dissolved in 2 mM HCl (1.6 L) at 80° C. in a large beaker. The solution was cooled to room temperature prior to the addition of Na[Ru$^{III}$Cl$_4$(Hind)$_2$](1.8 g, 3.40 mmol, 1 eq.) as an aqueous solution (400 mL H$_2$O). The resulting brownish-red colored solution was stirred for 5 min and then left to sit without stirring. After 1 day crystals began to form at the bottom of the beaker. After a total of 3 days a significant amount of crystals formed and were collected by vacuum filtration, washed with H$_2$O (2×350 mL), and dried overnight under reduced pressure to yield Ru$^{III}$Cl$_3$(Hind)$_2$(H$_2$O) (930 mg, 59.2%) as dark red crystals. The product was suitable for x-ray crystallography, which was used to confirm the structure.

Example 8—Preparation of Compound C

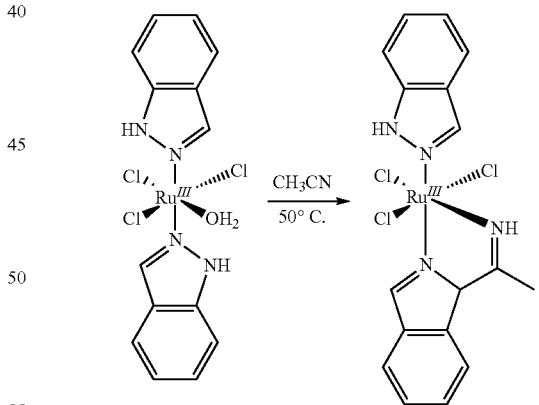

A 100 mL round-bottom flask fitted with a reflux condenser was charged with Ru$^{III}$Cl$_3$(Hind)$_2$(H$_2$O) (100 mg, 0.217 mmol) and CH$_3$CN (6 mL). The resulting dark red suspension was heated to 50° C. After a few hours the material solubilized and was left to stir at 50° C. After 4 days, noticeable precipitation had formed in the reaction flask. The crude reaction mixture was centrifuged to yield a dark brown solid, which was washed with cold Et$_2$O (3×, isolated each time via centrifugation). The resulting light brown powder was >95% pure (HPLC analysis). A small amount (~40 mg) of the product was dissolved in a minimal amount of CH$_3$CN (~20 mL), sonicated to dissolve, and then sealed in a vial. After 1-2 days, diffraction quality red crystals formed and the structure was confirmed by x-ray crystallography.

Example 9—Preparation of Compound D

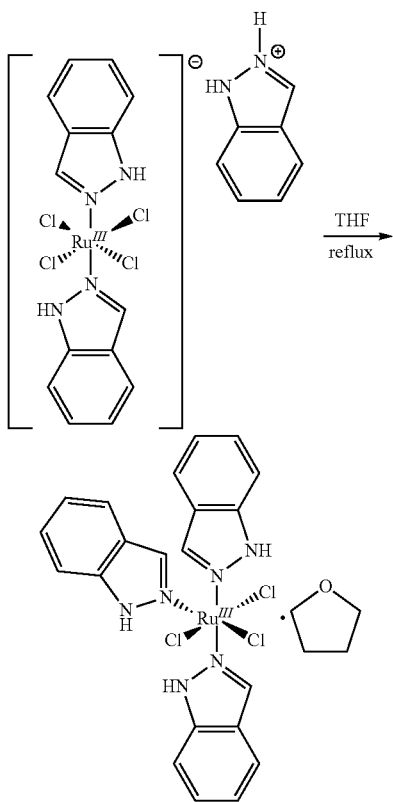

A 50 mL round-bottom flask fitted with a reflux condenser was charged with Hind[Ru$^{III}$Cl$_4$(Hind)$_2$](198 mg, 0.331 mmol) and THF (10 mL). The resulting brownish-red suspension was sonicated briefly to break-up a large chunks of material. The reaction mixture was heated to reflux; after 20 mins the material completely solubilized to yield a dark red solution. After an additional 20 mins at reflux, the reaction mixture was cooled to room temperature and aliquots of various volumes (0.1-1.0 mL were diluted with varying amount of Et$_2$O or MTBE (1-15 mL). After 1-2 days several crystallization trials had produced dark red crystals. The most successful attempts involved a dilution factor of 1:2-3 (i.e. 1 volume of reaction mixture diluted with 2-3 volumes of either Et$_2$O or MTBE). The crystals were washed with either cold Et$_2$O or cold MTBE depending on the anti-solvent used. This yielded red crystals, which were used to confirm the structure via x-ray crystallography.

Example 10—IT-139 Formulation Process

IT-139 was prepared chilled using cold (2-8° C.) solutions for a total volume of 1 L drug product. Citrate buffer was prepared by adding sodium citrate solution (29.4 g/L in water) to citric acid solution (19.2 g/L in water) until the pH was increased from 2.0 to 3.4. Working citrate buffer solution was then prepared by adding 33 mL citrate buffer in 767 mL water. 6.66 grams of sodium trans-[tetrachlorobis(1H-indazole)ruthenate (III)] was added to 800 mL of cold (2-8° C.) working citrate buffer solution and stirred using a magnetic stir plate and stir bar for 20 minutes while chilling the solution at 2-8° C. A working solution of mannitol was prepared by dissolving 13.3 g mannitol in 200 mL water. 100 mL of cold (2-8° C.) mannitol solution was added to the 800 mL of dissolved sodium trans-[tetrachlorobis(1H-indazole)ruthenate (III)] in working citrate buffer, and stirred for 5 minutes while chilling the solution at 2-8° C. 100 mL of cold (2-8° C.) water was added to the drug product solution for a final volume of 1 L. The IT-139 drug product bulk solution was filtered through a 0.22 µm pass through filter and aseptically filled into lyophilization vials for a final 30 mL fill in a 50 mL clear glass vial. The vials were partially stoppered and loaded into a lyophilizer with shelves precooled to −5° C. The lyophilization cycle consisted of freezing at −40° C. for 3 hours, primary drying at −10° C. for 15 hours at 0.1 mbar, followed by −5° C. for 10 hours at 0.1 mbar, and secondary drying at 5° C. for 2 hours at 0.05 mbar, followed by 10° C. for 2 hours at 0.05 mbar, followed by 15° C. for 2 hours at 0.05 mbar, followed by 20° C. for 2 hours at 0.05 mbar for a total drying time of 36 hours. Vials were fully stoppered, sealed, and stored at −20° C.

Example 11—IT-139 Formulation Process 2

The IT-139 was prepared chilled using cold (2-8° C.) solutions for a total volume of 2.8 L drug product. Citrate buffer was prepared by adding sodium citrate solution (29.4 g/L in water) to citric acid solution (19.2 g/L in water) until the pH was increased from 2.0 to 3.4. Working citrate buffer solution was then prepared by adding 9.3 g citrate buffer to 1960 g water. 36.3 g of sodium trans-[tetrachlorobis(1H-indazole)ruthenate (III)] was added to 1969.3 grams of cold (2-8° C.) working citrate buffer solution and stirred using a magnetic stir plate and stir bar for 20 minutes while chilling the solution at 2-8° C. A working solution of mannitol was prepared by dissolving 35 g mannitol in 525 mL water. 525 mL of cold (2-8° C.) mannitol solution was added to the solution of sodium trans-[tetrachlorobis(1H-indazole)ruthenate (III)] in working citrate buffer, and stirred for 5 minutes while chilling the solution at 2-8° C. 300 mL of cold (2-8° C.) water was added to the drug product solution for a final volume of 2.8 L. The IT-139 drug product bulk solution was filtered through a 0.22 µm pass through filter and aseptically filled into lyophilization vials for a final 25.1 gram fill in a 50 mL clear glass vial. The vials were partially stoppered and loaded into a lyophilizer with shelves precooled to −5° C. The lyophilization cycle consisted of freezing at −40° C. for 6 hours, primary drying at −10° C. for 50 hours at 0.2 mbar, and secondary drying at 30° C. for 33 hours at 0.2 mbar. Vials were backfilled with nitrogen, fully stoppered, sealed, and stored at 4° C.

Example 12—Batch Analysis of IT-139 Drug Substance

Batch analysis data for drug substance comprising sodium trans-[tetrachlorobis(1H-indazole)ruthenate (III)], Ru$^{III}$Cl$_3$(Hind)$_2$(H$_2$O), Ru$^{III}$Cl$_3$(Hind)$_2$(CH$_3$CN), Ru$^{III}$Cl$_3$(Hind)(HN=C(Me)ind) and cesium is reproduced in Table 8.

TABLE 8

Batch analysis data for drug substance comprising sodium trans-[tetrachlorobis(1H-indazole)ruthenate (III)], $Ru^{III}Cl_3(Hind)_2(H_2O)$, $Ru^{III}Cl_3(Hind)_2(CH_3CN)$, $Ru^{III}Cl_3(Hind)(HN=C(Me)ind)$ and cesium.

| Parameter | Acceptance Criteria | Results: Batch CB186/25 |
|---|---|---|
| 1. Characters | | |
| Appearance | Dark brown powder | Dark brown powder |
| 2. Identity | | |
| IR spectrum | Conforms to standard | — |
| HPLC retention time | Conforms to standard | Conforms to standard |
| 3. Tests | | |
| HPLC purity [% area] (dried basis) | NLT 95.5 | 97.46 |
| Assay Ruthenium [% wt.] (dried basis) | 19.12-21.14 | — |
| Assay Chlordie [% wt.] (dried basis) | 25.0-30.0 | 28.5 |
| Water content [% wt.] | NMT 7.0 | 6.64 |
| Assay Cesium [ppm] | NMT 5000 | 40 |
| Assay Aluminum [ppm] | NMT 100 | <5 |
| 4. Impurities | | |
| Indazole [% wt.] | NMT 0.25 | not detected |
| Impurity (Compound A) at RRT 1.09 (+/− 0.02) | NMT 1.0 | 0.63 |
| Impurity (Compound B) at RRT 1.28 (+/− 0.02) | NMT 2.5 | 0.93 |
| Impurity (Compound C) at RRT 1.06 (+/− 0.03) | NMT 2.0 | 0.66 |
| Any unspecified impurity [% area] | NMT 0.5 | 0.12 |
| Total Impurities [% area] | NMT 5.0 | 2.48 |
| 5. Residual Solvents | | |
| Acetonitrile [ppm] | NMT 410 | Not detected |
| Methanol [ppm] | NMT 3000 | Not detected |
| Ethanol [ppm] | NMT 5000 | Not detected |
| tert-Butyl metyl ether [ppm] | NMT 5000 | 815 |
| Methyl ethyl ketone [ppm] | NMT 5000 | 1562 |
| 6. Heavy Metals | | |
| Os [ppm] | NMT 10 | — |
| Si | Report results | — |
| 7. Microbial bioburden | | |
| Total aerobic microbial count [CFU/g] | NMT 20 | — |
| Total combined yeast and mold count [CFU/g] | NMT 5 | — |
| Bacterial endotoxins [EU/mg] | NMT 1.0 | — |

What is claimed is:

1. A method of treating a cancer in a subject in need thereof, comprising administering to the subject an effective amount of a composition comprising:
   a) sodium trans-[tetrachlorobis(1H-indazole)ruthenate (III)], sodium citrate, citric acid, and mannitol;
   b) mer,trans-[$Ru^{III}Cl_3(Hind)_2(H_2O)$]; and
   c) a cesium salt,
   wherein the sodium trans-[tetrachlorobis(1H-indazole)ruthenate (III)] is amorphous;
   wherein the subject is a human patient; and
   wherein the cancer is cancer of the pancreas, colon-rectum, stomach, or biliary passages.

2. The method of claim 1, wherein:
   mer,trans-[$Ru^{III}Cl_3(Hind)_2(H_2O)$] is between about 0.01 and about 0.4 weight percent of the composition, or between about 0.01 and about 0.3 weight percent of the composition, or between about 0.01 and about 0.2 weight percent of the composition;
   and cesium is between about 0.00001 and about 0.01 weight percent of the composition.

3. The method of claim 2, wherein:
   sodium trans-[tetrachlorobis(1H-indazole)ruthenate (III)] is about 40 to about 60 weight percent of the composition,
   mannitol is about 40 to about 60 weight percent of the composition,
   citric acid is about 0.01 to about 0.5 weight percent of the composition,
   and sodium citrate is about 0.001 to about 0.25 weight percentage of the composition.

4. The method of claim 3, wherein the composition further comprises $Ru^{III}Cl_3(Hind)_2(H_2O)$, $Ru^{III}Cl_3(Hind)_2(CH_3CN)$, and $Ru^{III}Cl_3(Hind)(HN=C(Me)ind)$.

5. The composition of claim 4, wherein:
   the $Ru^{III}Cl_3(Hind)_2(H_2O)$ is not more than about 0.5 weight percentage of the composition,
   the $Ru^{III}Cl_3(Hind)_2(CH_3CN)$ is not more than about 1.25 weight percentage of the composition,
   the $Ru^{III}Cl_3(Hind)(HN=C(Me)ind)$ is not more than about 1.0 weight percentage of the composition.

6. The method of claim 1, further comprising administering to the patient an effective amount of a chemotherapy agent.

7. The method of claim 6, wherein the chemotherapy agent is gemcitabine or oxaliplatin.

8. The method of claim 7, wherein the chemotherapy agent is oxaliplatin and the cancer is of the colon-rectum, stomach or biliary passages.

9. The method of claim 7, wherein the chemotherapy agent is gemcitabine and the cancer is of the pancreas.

* * * * *